United States Patent
Tang et al.

(10) Patent No.: US 11,191,734 B2
(45) Date of Patent: Dec. 7, 2021

(54) KETAMINE TRANSDERMAL DELIVERY SYSTEM

(71) Applicant: SHENOX PHARMACEUTICALS, LLC, McLean, VA (US)

(72) Inventors: Huadong Tang, McLean, VA (US); Hock S. Tan, East Brunswick, NJ (US); Michael Mayersohn, Marana, AZ (US)

(73) Assignee: SHENOX PHARMACEUTICALS, LLC, McLean, VA (US)

( * ) Notice: Subject to any disclaimer, the term of this patent is extended or adjusted under 35 U.S.C. 154(b) by 18 days.

(21) Appl. No.: 15/736,182

(22) PCT Filed: Jun. 27, 2016

(86) PCT No.: PCT/US2016/039601
§ 371 (c)(1),
(2) Date: Dec. 13, 2017

(87) PCT Pub. No.: WO2017/003935
PCT Pub. Date: Jan. 5, 2017

(65) Prior Publication Data
US 2018/0353437 A1 Dec. 13, 2018

Related U.S. Application Data

(60) Provisional application No. 62/185,573, filed on Jun. 27, 2015.

(51) Int. Cl.
| | |
|---|---|
| *A61K 9/70* | (2006.01) |
| *A61K 31/135* | (2006.01) |
| *A61P 25/24* | (2006.01) |
| *A61K 47/10* | (2017.01) |
| *A61K 47/12* | (2006.01) |
| *A61K 47/14* | (2017.01) |
| *A61K 47/32* | (2006.01) |

(52) U.S. Cl.
CPC .......... *A61K 9/7061* (2013.01); *A61K 9/7053* (2013.01); *A61K 31/135* (2013.01); *A61K 47/10* (2013.01); *A61K 47/12* (2013.01); *A61K 47/14* (2013.01); *A61K 47/32* (2013.01); *A61P 25/24* (2018.01)

(58) Field of Classification Search
CPC ...... A61K 31/135; A61K 47/14; A61K 47/10; A61K 47/12; A61K 47/32; A61P 25/24
See application file for complete search history.

(56) References Cited

U.S. PATENT DOCUMENTS

| | | | |
|---|---|---|---|
| 6,017,961 A | 1/2000 | Flores et al. | |
| 6,248,789 B1 | 6/2001 | Weg | |
| 6,855,735 B2 | 2/2005 | Friedman | |
| 7,638,651 B2 | 12/2009 | Gant et al. | |
| 7,645,767 B2 | 1/2010 | Singh et al. | |
| 7,687,080 B2 * | 3/2010 | Wolicki | A61K 31/24 424/400 |
| 7,973,043 B2 | 7/2011 | Migaly | |
| 8,137,711 B2 | 3/2012 | Wolicki | |
| 8,309,570 B2 | 11/2012 | Sang | |
| 8,629,184 B2 | 1/2014 | Wolicki et al. | |
| 8,741,332 B2 | 6/2014 | Zhang et al. | |
| 8,785,500 B2 | 7/2014 | Charney et al. | |
| 8,846,765 B2 | 9/2014 | Schiene et al. | |
| 9,073,819 B2 | 7/2015 | Amin et al. | |
| 9,650,352 B2 | 5/2017 | Wainer et al. | |
| 9,724,315 B2 * | 8/2017 | Ray, II | A61K 31/135 |
| 9,872,841 B2 | 1/2018 | Hashimoto | |
| 2003/0082225 A1 | 5/2003 | Mason | |
| 2004/0248964 A1 | 12/2004 | Crooks et al. | |
| 2004/0265364 A1 | 12/2004 | Ozturk et al. | |
| 2005/0148673 A1 | 7/2005 | Harbut et al. | |
| 2005/0222270 A1 | 10/2005 | Olney et al. | |
| 2010/0172946 A1 * | 7/2010 | Song | A61K 9/7061 424/402 |
| 2011/0065627 A1 | 3/2011 | Barathur et al. | |
| 2011/0178114 A1 * | 7/2011 | Aung-din | A61K 9/0014 514/282 |
| 2011/0313372 A1 * | 12/2011 | Eifler | A61K 31/13 604/304 |
| 2012/0225949 A1 | 9/2012 | Papalos | |
| 2012/0270916 A1 | 10/2012 | Wolicki | |

(Continued)

FOREIGN PATENT DOCUMENTS

| | | |
|---|---|---|
| CN | 101466364 A | 6/2009 |
| EP | 1562566 B1 | 6/2008 |

(Continued)

OTHER PUBLICATIONS

Bell et al., Perioperative ketamine for acute postoperative pain (Review); The Cochrane Collaboration. Published by John Wiley & Sons, Ltd 2010 (hereinafter Bell). (Year: 2010).*

Crowley et al., Clinical Application of Ketamine Ointment in the Treatment of Sympathetically Maintained Pain, International Journal of Pharmaceutical Compounding vol. 2 No. 2 Mar./Apr. 1998. (Year: 1998).*

Kotiyan et al., Eudragits: Role as crystallization inhibitors in drug-in-adhesive transdermal systems of estradiol, European Journal of Pharmaceutics and Biopharmaceutics 52 (2001) 173-180. (Year: 2001).*

(Continued)

Primary Examiner — Jessica Worsham
(74) Attorney, Agent, or Firm — Nixon & Vanderhye P.C.

(57) ABSTRACT

The present invention is directed to a transdermal delivery device comprising ketamine and formulations thereof. The present invention is also directed to a transdermal delivery device comprising ketamine for the treatment of major depressive disorder (MDD) and/or pain. The present invention is further directed to a transdermal delivery device comprising ketamine and abuse deterrent agents.

13 Claims, 8 Drawing Sheets

(56) References Cited

U.S. PATENT DOCUMENTS

| | | | |
|---|---|---|---|
| 2013/0165875 A1* | 6/2013 | Choi | A61K 9/7053 604/307 |
| 2013/0197041 A1 | 8/2013 | McCarthy et al. | |
| 2013/0209585 A1 | 8/2013 | Kim | |
| 2013/0211351 A1* | 8/2013 | Fuhrherr | A61K 9/7038 604/307 |
| 2013/0236573 A1 | 9/2013 | Singh et al. | |
| 2014/0057988 A1 | 2/2014 | Weg | |
| 2014/0079740 A1 | 3/2014 | Salama | |
| 2014/0093592 A1 | 4/2014 | Singh et al. | |
| 2014/0256821 A1 | 9/2014 | Charney et al. | |
| 2014/0275278 A1 | 9/2014 | Basstanie et al. | |
| 2015/0057317 A1 | 2/2015 | Mccarthy et al. | |
| 2015/0224070 A1 | 8/2015 | Boudy et al. | |
| 2015/0342947 A1 | 12/2015 | Pollard et al. | |
| 2016/0045455 A1 | 2/2016 | Drevets et al. | |
| 2016/0101069 A1 | 4/2016 | Charney et al. | |
| 2016/0199304 A1 | 7/2016 | Nivorozhkin et al. | |
| 2016/0256415 A1 | 9/2016 | Mccarty | |
| 2016/0338977 A1 | 11/2016 | Singh et al. | |
| 2017/0042878 A1 | 2/2017 | Fava et al. | |
| 2017/0049694 A1* | 2/2017 | Maalawy | A61K 47/24 |
| 2017/0181966 A1 | 6/2017 | Charney et al. | |
| 2017/0190653 A1 | 7/2017 | Sleigh et al. | |
| 2017/0231906 A1 | 8/2017 | Salce, Jr. et al. | |
| 2017/0266319 A1 | 9/2017 | Ueno et al. | |
| 2017/0348252 A1 | 12/2017 | Kent | |
| 2017/0355663 A1 | 12/2017 | Nivorozhkin et al. | |
| 2020/0030251 A1 | 1/2020 | Tang et al. | |

FOREIGN PATENT DOCUMENTS

| | | | |
|---|---|---|---|
| EP | 2932971 A1 | 10/2015 | |
| JP | 2010229045 A | 10/2010 | |
| JP | 2015501302 A | 1/2015 | |
| WO | WO-9707750 A1 * | 3/1997 | A61K 31/135 |
| WO | 2007111880 A2 | 10/2007 | |
| WO | 2013056229 A1 | 4/2013 | |
| WO | 2014169272 A1 | 10/2014 | |
| WO | WO-2015051259 A1 | 4/2015 | |
| WO | WO-2016109427 A1 | 7/2016 | |
| WO | WO-2016172672 A1 | 10/2016 | |
| WO | WO-2017041112 A1 | 3/2017 | |
| WO | WO-2017087691 A1 | 5/2017 | |
| WO | WO-2017139382 A1 | 8/2017 | |
| WO | WO-2017165877 A1 | 9/2017 | |
| WO | WO-2017165878 A1 | 9/2017 | |
| WO | WO-2017173442 A1 | 10/2017 | |
| WO | WO-2017180589 A1 | 10/2017 | |
| WO | WO-2017205666 A1 | 11/2017 | |
| WO | WO-2017208031 A1 | 12/2017 | |

OTHER PUBLICATIONS

Aan Het Rot, M., et al., "Safety and Efficacy of Repeated-dose Intravenous Ketamine for Treatment-resistant Depression," Biological Psychiatry, 67(2):139-145, Elsevier, United States (Jan. 2010).

Abdallah, C.G., et al., "The Neurobiology of Depression, Ketamine and Rapid-acting Antidepressants: Is It Glutamate Inhibition or Activation?," Pharmacology & Therapeutics, 190:148-158, Pergamon Press, England (Oct. 2018).

Amiaz, R., "Attenuation of Antidepressant Effects of Ketamine by Opioid Receptor Antagonism: Is It a Ketamine-Specific Effect?," 176(3):250-251, American Psychiatric Association (Mar. 2019).

Anderson, I.M., et al., "Randomised Controlled Trial of Ketamine Augmentation of Electroconvulsive Therapy to Improve Neuropsychological and Clinical Outcomes in Depression (Ketamine-ECT Study)," Efficacy and Mechanism Evaluation, 4(2):138, National Institute for Health Research (Mar. 2017).

Aust, S., et al., "Anxiety During Ketamine Infusions Is Associated With Negative Treatment Responses in Major Depressive Disorder.," European Neuropsychopharmacology, 29(4):529-538, Elsevier, Netherlands (Apr. 2019).

Azevedo, V.M.S., et al., "Transdermal Ketamine as an Adjuvant for Postoperative Analgesia After Abdominal Gynecological Surgery Using Lidocaine Epidural Blockade," Anesthesia & Analgesia, 91(6):1479-1482, Baltimore, Lippincott Williams & Wilkins (Dec. 2000).

Bartoli, F., et al., "Antidepressant Response and Dissociative Effects After Ketamine Treatment: Two Sides of the Same Coin?," The Journal of Clinical Psychiatry, 78(9):e1318, Memphis, Physicians Postgraduate Press (Dec. 2017).

Bartoli ,F., et al., "Ketamine for suicidal ideation treatment: Available evidence remains convincing.," Neuroscience and biobehavioral reviews, 99:1-2, Pergamon Press,United States (Apr. 2019).

Bronsky, E.S., et al., "Intravenous Low-Dose Ketamine Provides Greater Pain Control Compared to Fentanyl in a Civilian Prehospital Trauma System: A Propensity Matched Analysis," National Association of EMS Physicians, 18:1-8, Philadelphia, Hanley & Belfus (May 2018).

Can, A., et al., "Effects of Ketamine and Ketamine Metabolites on Evoked Striatal Dopamine Release, Dopamine Receptors, and Monoamine Transporters," The Journal of Pharmacology and Experimental Therapeutics, 359(1):159-170, American Society for Pharmacology and Experimental Therapeutics, United States (Oct. 2016).

Canadian Agency for Drugs and Technologies in Health, "Intravenous Ketamine for the Treatment of Mental Health Disorders: A Review of Clinical Effectiveness and Guidelines," 24 pages, Ottawa (Aug. 2014).

Chaki, S., and Yamaguchi, J.I., "Is the History Repeated? Can (2R,6R)-Hydroxynorketamine be Another Antidepressant?," Journal of Experimental Neuroscience, 12:1, SAGE Publications, United States (Dec. 2018).

Chaki, S., "Is Metabolism of (R)-Ketamine Essential for the Antidepressant Effects?," The International Journal of Neuropsychopharmacology, 21(2):154-156, Oxford University Press (Feb. 2018).

Chang, L., et al., "Comparison of Antidepressant and Side Effects in Mice After Intranasal Administration of (R,S)-ketamine, (R)-ketamine, and (S)-ketamine," Pharmacology, Biochemistry, and Behavior, 181:53-59, Elsevier, United States (Apr. 2019).

Chen, I.C., et al., "Risk Factors of Lower Urinary Tract Syndrome among Ketamine Users," Lower Urinary Tract Symptoms, 10(3):281-286, Blackwell Publishing Asia, Australia (Sep. 2018).

Chen, M.H., et al., "Antisuicidal Effect, Bdnf Val66met Polymorphism, and Low-dose Ketamine Infusion: Reanalysis of Adjunctive Ketamine Study of Taiwanese Patients With Treatmen-tresistant Depression (AKSTP-TRD)," Journal of Affective Disorders, 251:162-169, Elsevier/North-Holland Biomedical Press, Netherlands (May 2019).

Clements, J.A., et al., "Bioavailability, Pharmacokinetics, and Analgesic Activity of Ketamine in Humans," Journal of Pharmaceutical Sciences, 71(5):539-542, New York, Elsevier (May 1982).

Cohen, I.V., et al., "Population Scale Data Reveals the Antidepressant Effects of Ketamine and Other Therapeutics Approved for Non-psychiatric Indications," Scientific Reports, 7(1):1450, Nature Publishing Group, England (May 2017).

Continuation Phase Intravenous Ketamine in Adults With Treatment-Resistant Depression, Clinical Trials, ACNP 55th Annual Meeting, 2 pages.

Cooper, M,D., et al., "Strategies to Mitigate Dissociative and Psychotomimetic Effects of Ketamine in the Treatment of Major Depressive Episodes: a Narrative Review," The World Journal of Biological Psychiatry, 18(6):410-423, London, Informa Healthcare (Sep. 2017).

Correia-Melo, F.S., et al., "Rapid Infusion of Esketamine for Unipolar and Bipolar Depression: A Retrospective Chart Review," Neuropsychiatric Disease and Treatment, 13:1627-1632, Albany, Auckland (Jun. 2017).

Correll, G.E., et al., "Subanesthetic Ketamine Infusion Therapy: a Retrospective Analysis of a Novel Therapeutic Approach to Complex Regional Pain Syndrome," Pain Medicine, 5(3):263-275, Oxford, England, Oxford University Press on behalf of the American Academy of Pain Medicine (Sep. 2004).

(56) References Cited

OTHER PUBLICATIONS

Cowen, P.J., "Backing into the Future: Pharmacological Approaches to the Management of Resistant Depression," Psychological Medicine, 47(15):2569-2577, London, Cambridge University Press (Aug. 2017).

Cui ,Y., et al., "Decoding Depression: Insights from Glial and Ketamine Regulation of Neuronal Burst Firing in Lateral Habenula.," Cold Spring Harbor symposia on quantitative biology, 10 pages, Cold Spring Harbor Laboratory Press,United States (Feb. 2019).

Curran, H.V., and Morgan, C., "Cognitive, Dissociative and Psychotogenic Effects of Ketamine in Recreational Users on the Night of Drug Use and 3 Days Later," Addiction, 95(4):575-590, Wiley-Blackwell, England (Apr. 2000).

Daly, EJ., et al., "Efficacy and Safety of Intranasal Esketamine Adjunctive to Oral Antidepressant Therapy in Treatment-Resistant Depression: A Randomized Clinical Trial," JAMA Psychiatry, 75(2):139-148, Chicago, American Medical Association (Feb. 2018).

Defense Health Program Fiscal Year (FY) 2017 Budget Estimates Operation and Maintenance, 625 pages, Research, Development, Test and Evaluation (Feb. 2016).

Charney, D. and Feder, A., "Ketamine as a Rapid Treatment in Post-traumatic Stress Disorder," Mount Sinai School of Medicine, Oct. 2012, 5 pages.

Department of Defense, VA/DoD Clinical Practice Guideline for the Management of Major Depressive Disorder, 173 pages, (Apr. 2016).

Desta, Z., et al., "Stereoselective and Regiospecific Hydroxylation of Ketamine and Norketamine," Xenobiotica, 42(11):1076-1087, Informa Healthcare, England (Nov. 2012).

Deyama, S., et al., "Neurotrophic and Antidepressant Actions of Brain-Derived Neurotrophic Factor Require Vascular Endothelial Growth Factor," Biological Psychiatry (Dec. 2018).

DHB Memo 120308 Ketamine, 23 pages, Prehospital Use of Ketamine in Battlefield Analgesia (Mar. 2012).

Diazgranados, N., et al., "A Randomized Add-on Trial of an N-methyl-D-aspartate Antagonist in Treatment-Resistant Bipolar Depression," Archives of General Psychiatry, 67(8):793-802, Chicago, American Medical (Aug. 2010).

Dinis-Oliveira, R.J., "Metabolism and Metabolomics of Ketamine: a Toxicological Approach," Forensic Sciences Research, 2(1):2-10, Taylor & Francis Group, England (Feb. 2017).

Duman, R.S., "The Dazzling Promise of Ketamine," Cerebrum, 13 pages, (Mar. 2018).

Dutta, A., et al., "Ketamine and Other Potential Glutamate Antidepressants," Psychiatry Research, 225(1-2):1-13, Limerick, Elsevier (Jan. 2015).

Esketamine Nasal Spray for Patients with Treatment-resistant Depression, Advisory Committee Briefing Document, JNJ-54135419, Janssen Research & Development, LLC (Jan. 2019).

Fallon, M.T., et al., "Oral Ketamine vs Placebo in Patients With Cancer-Related Neuropathic Pain: A Randomized Clinical Trial," JAMA Oncology, 4(6):870-872, Chicago II, American Medical Association (Apr. 2018).

Fanta, S., et al., "Population Pharmacokinetics of S-ketamine and Norketamine in Healthy Volunteers After Intravenous and Oral Dosing," European Journal of Clinical Pharmacology, 71(4):441-447, Berlin, New York, Springer (Apr. 2015).

Fond, G., et al., "Ketamine Administration in Depressive Disorders: a Systematic Review and Meta-analysis," Psychopharmacology, 231(18):3663-3676, Berlin, New York (Sep. 2014).

Fukumoto, K., et al., "Antidepressant Potential of (R)-Ketamine in Rodent Models: Comparison with (S)-Ketamine," Journal of Pharmacology and Experimental Therapeutics, 361 (1):9-16, American Society for Pharmacology and Experimental Therapeutics, United States (Apr. 2017).

Galvez Ortiz, V., et al., "A Reply to Comments by Lee and Colleagues on: Repeated Intranasal Ketamine for Treatment Resistant Depression—The Way to Go? Results from a Pilot Randomised Controlled Trial," Journal of Psychopharmacology, 33(2):260-261, Thousand Oaks, Sage Publications (Feb. 2019).

Geisslinger, G., et al., "Pharmacokinetics and Pharmacodynamics of Ketamine Enantiomers in Surgical Patients Using a Stereoselective Analytical Method," British Journal of Anaesthesia, 70(6):666-671, Elsevier, England (Jun. 1993).

Goldberg, M.E., et al., "Enantioselective Pharmacokinetics of (R)- and (S)-ketamine After a 5-day Infusion in Patients With Complex Regional Pain Syndrome," Chirality, 23(2):138-143, New York, Wiley (Feb. 2011).

Gottlieb, M., et al., "Is Low-Dose Ketamine an Effective Alternative to Opioids for the Treatment of Acute Pain in the Emergency Department?," Annals of Emergency Medicine, 72(2):133-134, St. Louis, Mosby (Dec. 2017).

Halberstadt, A.L., et al., "The Novel Ketamine Analog Methoxetamine Produces Dissociative-like Behavioral Effects in Rodents," Journal of Psychopharmacology, 233(7):1215-1225, Springer-Verlag, Germany (Apr. 2016).

Hartvig, P., et al., "Postoperative Analgesia and Sedation Following Pediatric Cardiac Surgery Using a Constant Infusion of Ketamine," Journal of Cardiothoracic and Vascular Anesthesia, 7(2):148-153, Philadelphia, PA, W.B. Saunders (Apr. 1993).

Hasin, D.S., et al., "Epidemiology of Major Depressive Disorder: Results From the National Epidemiologic Survey on Alcoholism and Related Conditions," Archives of General Psychiatry, 62(10):1097-1106, Chicago, American Medical Assn (Oct. 2005).

Hasselmann, H.W., "Ketamine as Antidepressant? Current State and Future Perspectives," Current Neuropharmacology, 12(1):57-70, Sharjah, U.A.E., San Francisco, CA, Bentham Science Publishers (Jan. 2014).

Heifets ,B.D., et al., "Interpreting Ketamine's Opioid Receptor Dependent Effect: Response to Sanacora," The American journal of psychiatry, 176(3):249-250, American Psychiatric Association,United States (Mar. 2019).

Herzog ,D.P., et al., "Decoding the Mechanism of Action of Rapid-acting Antidepressant Treatment Strategies: Does Gender Matter?," International Journal of Molecular Sciences, 20(4):949, Switzerland : MDPI, [2000—,Switzerland (Feb. 2019).

Hong, Y.L., et al., "Management of Complications of Ketamine Abuse: 10 years' Experience in Hong Kong," Hong Kong Medical Journal, 24(2):175-181, Hong Kong, Academy of Medicine Press (Apr. 2018).

Ibrahim, L., et al., "Course of Improvement in Depressive Symptoms to a Single Intravenous Infusion of Ketamine Vs Add-on Riluzole: Results From a 4-week, Double-blind, Placebo-controlled Study," Neuropsychopharmacology, 37(6):1526-1533, Nature Publishing Group, England (May 2012).

Ide, S., et al., "Role of NMDA Receptor GluN2D Subunit in the Antidepressant Effects of Enantiomers of Ketamine," Journal of Pharmacological Sciences, 135(3):138-140, Japanese Pharmacological Society, Japan (Nov. 2017).

Joint Trauma System Clinical Practice Guideline (JTS CPG), 24 pages, Pain, Anxiety and Delirium (Mar. 2017).

Jonkman, K., et al., "Ketamine for Cancer Pain: What Is the Evidence?," Current Opinion in Supportive and Palliative Care, 11(2):88-92, Lippincott Williams & Wilkins, United States (Jun. 2017).

Kalin, N.H., "Improving the Lives of Patients With Major Depression by Focusing on New Treatment Approaches.," The American journal of psychiatry, 176(5):329-330, American Psychiatric Association,United States (May 2019).

Kaplan, M.S., et al., "Faculty of Pain Medicine,Anzca Annual Meeting Abstracts," Pain Medicine, 7(5):466-469, American Academy of Pain Medicine (2006).

Lee, K.K.C., Pharmacology of MDMA, Ketamine and Methamphetamine, 30 pages.

Ketalar (ketamine hydrochloride) injection CIII for intravenous and intramuscular use, Reference ID: 4303143, 10 Pages.

Ketamine: a review of use and harm, 48 pages, Advisory Council on the Misuse of Drugs (Dec. 2013).

Ketamine Critical Review Report, Expert Committee on Drug Dependence, 90 pages, Agenda item 4.2 (Jun. 2012).

Ketamine Update Review Report Agenda item 6.2, Expert Committee on Drug Dependence 36th ECDD Meeting, Jun. 2014, 45 pages.

(56) References Cited

OTHER PUBLICATIONS

Kim, J., and Mierzwinski-Urban, M., "Ketamine for Treatment-Resistant Depression or Post-Traumatic Stress Disorder in Various Settings: A Review of Clinical Effectiveness, Safety, and Guidelines," Canadian Agency for Drugs and Technologies in Health, 30 pages, Ottawa (Mar. 2017).

Klaess, C.C., et al., "Current Ketamine Practice: Results of the 2016 American Society of Pain Management Nursing Survey on Ketamine," American Society of Pain Management Nurses, 19(3):222-229, Philadelphia : WB Saunders (Jun. 2018).

Kraus, C., et al., "Gnosis and Improved Outcomes in Major Depression: A Review," Translational Psychiatry, 9(1):127, New York, Nature Pub. Group (Apr. 2019).

Krystal, J.H., et al., "Ketamine: A Paradigm Shift for Depression Research and Treatment," Neuron, 101(5):774-778, Cambridge, Cell Press (Mar. 2019).

Krystal, J.H., et al., "Synaptic Loss and the Pathophysiology of PTSD: Implications for Ketamine as a Prototype Novel Therapeutic," Current Psychiatry Reports, 19(10):74, Current Science, United States (Aug. 2017).

Krystal, J.H., PTSD: From neurobiology to treatment VA National Center for PTSD, Yale University, 62 pages.

Lai, R., et al., "Pilot Dose-Response Trial of i.v. Ketamine in Treatment-Resistant Depression," The World Journal of Biological Psychiatry, 15(7):579-584, London, Informa Healthcare (Apr. 2014).

Lapidus, K.A., et al., "A Randomized Controlled Trial of Intranasal Ketamine in Major Depressive Disorder," Biological Psychiatry, 76(12):970-976, New York, Elsevier (Dec. 2014).

Lara, D.R., et al., "Antidepressant, Mood Stabilizing and Procognitive Effects of Very Low Dose Sublingual Ketamine in Refractory Unipolar and Bipolar Depression," International Journal of Neuropsychopharmacology, 16(9):2111-2117, Oxford University Press (Oct. 2013).

Lauretti, G.R., et al., "Transdermal Ketamine and S(+)-Ketamine as Adjuvants Following Orthopaedic Surgery under Bupivacaine Spinal Anaesthesia," Journal of Physical Chemistry and Biophysics, 4(4):1000154, (Aug. 2014).

Lee, V., et al., "A Response to: Repeated Intranasal Ketamine for Treatment Resistant Depression: the Way to Go? Results From a Pilot Randomised Controlled Trial," Journal of Psychopharmacology, 33(2):258-259, (2019).

Liu, Y., et al., "Ketamine Abuse Potential and Use Disorder," Brain Research Bulletin, 126(Pt1):68-73, New York, Elsevier Science (Sep. 2016).

Luckenbaugh, D.A., et al., "Do the dissociative Side effects of ketamine mediate its antidepressant effects?," Journal of affective disorders, 159:56-61, Amsterdam, Elsevier (Apr. 2014).

Lumsden, E.W., et al., "Antidepressant-Relevant Concentrations of the Ketamine Metabolite (2R,6R)-Hydroxynorketamine Do Not Block NMDA Receptor Function," Proceedings of the National Academy of Sciences of the United States of America, 116(11):5160-5169, Washington, National Academy of Sciences (Feb. 2019).

Mahar Doan, K.M., et al., "Passive Permeability and P-glycoprotein-mediated Efflux Differentiate Central Nervous System (CNS) and Non-CNS Marketed Drugs," Journal of Pharmacology and Experimental Therapeutics, 303(3):1029-1037, American Society for Pharmacology and Experimental Therapeutics, United States (Dec. 2002).

Mahshidfar, B., et al., "Acute Pain Management in Emergency Department, Low Dose Ketamine Versus Morphine, A Randomized Clinical Trial," Anesthesiology and Pain Medicine, 7(6):e60561, Kowsar Corporation, Netherlands (Dec. 2017).

Niciu, M.J., et al., "Glutamate Receptor Antagonists as Fast-Acting Therapeutic Alternatives for the Treatment of Depression: Ketamine and Other Compounds," Annual Review of Pharmacology and Toxicology, 54:119-139, Annual Reviews, United States (2014).

Martinowich, K., et al., "Rapid Antidepressant Effects: Moving Right Along," Molecular Psychiatry, 18(8):856-863, Basingstoke, UK, Nature Publishing Group Specialist Journals (Aug. 2013).

Mion, G., "History of Anaesthesia: The Ketamine Story—Past, Present and Future," European Journal of Anaesthesiology, 34(9):571-575, Cambridge, Lippincott Williams (Sep. 2017 ).

Moaddel, R., et al., "The Distribution and Clearance of (2S,6S)-Hydroxynorketamine, An Active Ketamine Metabolite, in Wistar Rats," Pharmacology Research & Perspectives, 3(4):e00157, British Pharmacological Society (Aug. 2015).

Moaddel, R., et al., "Sub-Anesthetic Concentrations of (R,S)-Ketamine Metabolites Inhibit Acetylcholine-Evoked Currents in $\alpha 7$ Nicotinic Acetylcholine Receptors," European Journal of Pharmacology, 698(1-3):228-234, Amsterdam, Elsevier Science (Jan. 2013).

Moda-Sava, R.N., et al., "Sustained Rescue of Prefrontal Circuit Dysfunction by Antidepressant-induced Spine Formation," Science , 364(6436):eaat8078, American Association for the Advancement of Science, United States (Apr. 2019).

Morris, P.J., et al., "Synthesis and N-Methyl-D-aspartate (NMDA) Receptor Activity of Ketamine Metabolites," Organic Letters, 19(17):4572-4575, Washington, American Chemical Society (Sep. 2017).

Muller, J., et al., "Ketamine Enantiomers in the Rapid and Sustained Antidepressant Effects," Therapeutic Advances in Psychopharmacology, 6(3):185-192, London, Sage (Jun. 2016).

Murrough, J.W., et al., "Antidepressant Efficacy of Ketamine in Treatment-resistant Major Depression: a Two-site Randomized Controlled Trial," The American Journal of Psychiatry, 170(10):1134-1142, Arlington, VA, American Psychiatric Association (Oct. 2013).

Murrough, J.W., et al., "Neurocognitive Effects of Ketamine in Treatment-resistant Major Depression: Association With Antidepressant Response," Psychopharmacology, 231:481-488, 2014).

Murrough, J.W., et al., "Rapid and Longer-Term Antidepressant Effects of Repeated Ketamine Infusions in Treatment-Resistant Major Depression," Biological Psychiatry, 3 pages, New York, Elsevier, Supplemental Information (2013).

Murrough, J.W., et al., "Rapid and Longer-term Antidepressant Effects of Repeated Ketamine Infusions in Treatment-resistant Major Depression," Biological Psychiatry, 74(4):250-256, Elsevier, United States (Jul. 2012).

Murrough, J.W., "Ketamine as a Novel Antidepressant: From Synapse to Behavior," Clinical Pharmacology and Therapeutics, 91(2):303-309, Hoboken, NJ, Wiley (Feb. 2012).

Naidoo,V., et al., "Brain Penetration of Ketamine: Intranasal Delivery Vs Parenteral Routes of Administration.," Journal of Psychiatric Research, 112:7-11, Pergamon Press, England (May 2019).

Naughton, M., et al., "A Review of Ketamine in Affective Disorders: Current Evidence of Clinical Efficacy, Limitations of Use and Pre-clinical Evidence on Proposed Mechanisms of Action," Journal of Affective Disorders, 156:24-35, Elsevier/North-Holland Biomedical Press, Netherlands (Mar. 2014).

Neehoff, S., et al., "Dissociation After Ketamine Dosing: Is the CADSS Fit for Purpose?," Journal of Affective Disorders, 244:239-240, Amsterdam, Elsevier (Nov. 2017).

Newport, D.J., et al., "Ketamine and Other NMDA Antagonists: Early Clinical Trials and Possible Mechanisms in Depression," The American Journal of Psychiatry, 172(10):950-966, American Psychiatric Association, United States (Oct. 2015).

Ni, A., et al., "Ketamine Exposure Demographics and Outcomes Over 16 Years as Reported to US Poison Centers," The American Journal of Emergency Medicine, 36(8):1459-1462, Philadelphia, W B Saunders (May 2018).

Niciu, M.J., et al., "Clinical Predictors of Ketamine Response in Treatment-Resistant Major Depression," The Journal of Clinical Psychiatry, 75(5):e417-e423, Physicians Postgraduate Press, United States (May 2014).

Niciu, M.J., et al., "Features of Dissociation Differentially Predict Antidepressant Response to Ketamine in Treatment-Resistant Depression," Journal of Affective Disorders, 232:310-315, Amsterdam, Elsevier (Feb. 2018).

Niciu, M.J., et al., "Ketamine's Antidepressant Efficacy Is Extended for at Least Four Weeks in Subjects With a Family History of an Alcohol Use Disorder," The International Journal of Neuropsychopharmacology, 18(1):13, Oxford, Oxford University Press (Oct. 2014).

(56) References Cited

OTHER PUBLICATIONS

Nielsen, R.V., et al., "Intraoperative Ketamine Reduces Immediate Postoperative Opioid Consumption After Spinal Fusion Surgery in Chronic Pain Patients With Opioid Dependency: a Randomized, Blinded Trial," Pain, 158(3):463-470, Lippincott Williams & Wilkins, United States (Mar. 2017).
Niesters, M and Dahan, A., "Pharmacokinetic and Pharmacodynamic Considerations for NMDA Receptor Antagonists in the Treatment of Chronic Neuropathic Pain," Expert Opinion on Drug Metabolism & Toxicology, 8(11):1409-1417, Informa Healthcare, England (Nov. 2012).
Niesters, M., et al., "Ketamine for Chronic Pain: Risks and Benefits," British Journal of Clinical Pharmacology, 77(2):357-367, Oxford, Wiley-Blackwell (Feb. 2014).
Noppers, I., et al., "Effect of Rifampicin on S-ketamine and S-norketamine Plasma Concentrations in Healthy Volunteers after Intravenous Sketamine Administration," Anesthesiology, 114(6):1435-1445, Lippincott Williams & Wilkins, United States (Jun. 2011).
Paul, R.K., et al., "(R,S)-Ketamine Metabolites (R,S)-Norketamine and (2S,6S)-Hydroxynorketamine Increase the Mammalian Target of Rapamycin Function," The Journal of the American Society of Anesthesiologists, 121 (1):149-159, Philadelphia PA, Lippincott Williams & Wilkins (Jul. 2014).
Peltoniemi, M.A., et al., "Rifampicin has a Profound Effect on the Pharmacokinetics of Oral S-Ketamine and Less on Intravenous S-Ketamine," Basic & Clinical Pharmacology & Toxicology, 111(5):325-332, Blackwell, England (Nov. 2012).
Persson, J., et al., "Pharmacokinetics and Non-Analgesic Effects of S- and R-ketamines in Healthy Volunteers With Normal and Reduced Metabolic Capacity," European Journal of Clinical Pharmacology, 57(12):869-875, Springer, Germany (Feb. 2002).
Pham, T.H., et al., "Common Neurotransmission Recruited in (R,S)-Ketamine and (2R,6R)-Hydroxynorketamine-Induced Sustained Antidepressant-Like Effects," Biological Psychiatry, 84(1):e1-e4, New York, Elsevier (Jul. 2018).
Phillips, J.L., et al., "Single, Repeated, and Maintenance Ketamine Infusions for Treatment-resistant Depression: a Randomized Controlled Trial," The American Journal of Psychiatry, 176(5):401-409, American Psychiatric Association, United States (May 2019).
Pochwat, B., et al., "NMDA Antagonists Under Investigation for the Treatment of Major Depressive Disorder," Expert Opinion on Investigational Drugs, 23(9):1181-1192, Taylor & Francis, England (Sep. 2014).
Price, R.B., et al., "Effects of Ketamine on Explicit and Implicit Suicidal Cognition: a Randomized Controlled Trial in Treatment-resistant Depression," Depression and Anxiety, 31(4):335-343, New York, Wiley (Apr. 2014).
Psychopharmacologic Drugs Advisory Committee (PDAC) and Drug Safety and Risk Management (DSaRM) Advisory Committee Meeting, FDA UCM630970 (Feb. 2019).
Rasmussen, K.G., et al., "Serial Infusions of Low-Dose Ketamine for Major Depression," Journal of Psychopharmacology, 27(5):444-450, Thousand Oaks, Sage Publications (Feb. 2013).
Report on the risk assessment of ketamine in the framework of the joint action on new synthetic drugs, Office for Official Publications of the European Communities, 116, Luxembourg (2002).
Rigo, F.K., et al., "Management of Neuropathic Chronic Pain with Methadone Combined with Ketamine: A Randomized, Double Blind, Active-Controlled Clinical Trial," Pain Physician Journal, 20(3):207-215, American Society of Interventional Pain Physicians, United States (Mar. 2017).
Rodriguez, C.I., et al., "Challenges in Testing Intranasal Ketamine in Obsessive-Compulsive Disorder," The Journal of Clinical Psychiatry, 78(4):466-467, Physicians Postgraduate Press, United States (Apr. 2017).
Rybakowski, J.K., et al., "Ketamine Augmentation Rapidly Improves Depression Scores in Inpatients With Treatment-resistant Bipolar Depression," International Journal of Psychiatry in Clinical Practice, 21 (2):99-103, Informa Healthcare, England (Jun. 2017 ).

Sanacora, G., "Caution Against Overinterpreting Opiate Receptor Stimulation as Mediating Antidepressant Effects of Ketamine.," The American journal of psychiatry, 176(3):249, American Psychiatric Association, United States (Mar. 2019).
Sanacora, G., et al., "A Consensus Statement on the Use of Ketamine in the Treatment of Mood Disorders," JAMA Psychiatry, 74(4):399-405, American Medical Association, United States (Apr. 2017).
Schak, K.M., et al., "Potential Risks of Poorly Monitored Ketamine Use in Depression Treatment," The American Journal of Psychiatry, 173(3):215-218, American Psychiatric Association, United States (Mar. 2016).
Schatzberg, A.F., "Scientific Issues Relevant to Improving the Diagnosis, Risk Assessment, and Treatment of Major Depression," The American Journal of Psychiatry, 176(5):342-347, American Psychiatric Association, United States (May 2019).
Schwenk, E.S., et al., "Consensus Guidelines on the Use of Intravenous Ketamine Infusions for Acute Pain Management From the American Society of Regional Anesthesia and Pain Medicine, the American Academy of Pain Medicine, and the American Society of Anesthesiologists," Regional Anesthesia and Pain Medicine, 43(5):456-466, BMJ, England (Jul. 2018).
Shaffer, C.L., et al., "Enhancing Ketamine Translational Pharmacology via Receptor Occupancy Normalization," Neuropharmacology, 86:174-180, Pergamon Press, England (Nov. 2014).
Sheehy, K.A., et al., "Subanesthetic Ketamine for Pain Management in Hospitalized Children, Adolescents, and Young Adults: a Single-center Cohort Study," Journal of Pain Research, 10:787-795, Dove Medical Press, New Zealand (Apr. 2017).
Shirayama, Y., and Hashimoto, K., "Lack of Antidepressant Effects of (2R,6R)-hydroxynorketamine in a Rat Learned Helplessness Model: Comparison With (R)-ketamine," The International Journal of Neuropsychopharmacology, 21(1):84-88, Oxford, Oxford University Press (Jan. 2018).
Shiroma, P.R., et al., "Augmentation of Response and Remission to Serial Intravenous Subanesthetic Ketamine in Treatment Resistant Depression," Journal of Affective Disorders, 155:123-129, Elsevier/North-Holland Biomedical Press, Netherlands (Feb. 2014).
Shiroma, P.R., et al., "Neurocognitive Performance and Serial Intravenous Subanesthetic Ketamine in Treatment-resistant Depression," The International Journal of Neuropsychopharmacology, 17(11):1805-1813, Oxford Oxford University Press, England (Nov. 2014).
Sigtermans, M., et al., "S(+)-ketamine Effect on Experimental Pain and Cardiac Output: a Population Pharmacokinetic-pharmacodynamic Modeling Study in Healthy Volunteers," Anesthesiology, 111(4):892-903, Lippincott Williams & Wilkins, United States (Oct. 2009).
Sin, B., et al., "The Use of Ketamine for Acute Treatment of Pain: A Randomized, Double-Blind, Placebo-Controlled Trial," The Journal of Emergency Medicine, 52(5):601-608, Elsevier, United States (May 2017).
Singh, J.B., et al., "Intravenous Esketamine in Adult Treatment-Resistant Depression: A Double-Blind, Double-Randomization, Placebo-Controlled Study," Biological Psychiatry, 80(6):424-431, New York, Elsevier (Nov. 2015).
Singh, N.S., et al., "What Is Hydroxynorketamine and What Can It Bring to Neurotherapeutics?," Expert Review of Neurotherapeutics, 14(11):1239-1242, Taylor & Francis, England (Nov. 2014).
Soleimani, L., et al., "Does Ketamine Have Rapid Anti-Suicidal Ideation Effects?," Current Treatment Options in Psychiatry, 2(4):383-393, Springer International Publishing AG, Switzerland (Dec. 2015).
Spravato, Esketamine Nasal Spray Approved for Treatment-Resistant Depression (2019), 41 pages.
Strasburger, S.E., et al., "What Is the Mechanism of Ketamine's Rapid-onset Antidepressant Effect? A Concise Overview of the Surprisingly Large Number of Possibilities," Journal of Clinical Pharmacy and Therapeutics, 42(2):147-154, Wiley-Blackwell Pub, England (Apr. 2017).
The Implementation of a Comprehensive Policy on Pain Management by the Military Health Care System, 30 pages, Office of the Secretary of Defense (Oct. 2012).
Tse, Y.C., et al., "The Susceptibility to Chronic Social Defeat Stress is Related to Low Hippocampal Extrasynaptic NMDA Receptor

(56) References Cited

OTHER PUBLICATIONS

Function," Neuropsychopharmacology, 44(7):1310-1318, London, Nature Publishing Group (Jan. 2019).
Turfus, S.C., et al., "Use of Human Microsomes and Deuterated Substrates: an Alternative Approach for the Identification of Novel Metabolites of Ketamine by Mass Spectrometry," Drug Metabolism and Disposition, 37(8):1769-1778, American Society for Pharmacology and Experimental Therapeutics, United States (Aug. 2009).
Wang, M., and Kaplin, A., "Explaining Naltrexone's Interference With Ketamine's Antidepressant Effect," The American journal of psychiatry, 176(5):410-411, American Psychiatric Association, United States (May 2019).
White, M., et al., "Pharmacokinetics of S(+) Ketamine Derived From Target Controlled Infusion," British Journal of Anaesthesia, 96(3):330-334, Elsevier, England (Mar. 2006).
Wilkinson, ST., et al., "Impact of Midazolam vs. Saline on Effect Size Estimates in Controlled Trials of Ketamine as a Rapid-Acting Antidepressant," Neuropsychopharmacology, 44(7):1233-1238, London, Nature Publishing Group (Jan. 2019).
Xu, Y., et al., "Effects of Low-Dose and Very Low-Dose Ketamine among Patients with Major Depression: A Systematic Review and Meta-Analysis," International Journal of Neuropsychopharmacology, 19(4):1-15, Oxford University Press (Nov. 2015).
Yamaguchi, J., et al., "(2R,6R)-Hydroxynorketamine is Not Essential for the Antidepressant Actions of (R)-Ketamine in Mice," Neuropsychopharmacology, 43(9):1900-1907, London, Nature Publishing Group (May 2018).
Yanagihara, Y., et al., "Plasma Concentration Profiles of Ketamine and Norketamine after Administration of Various Ketamine Preparations to Healthy Japanese Volunteers," Biopharmaceutics & Drug Disposition, 24(1):37-43, Chichester, Wiley (Jan. 2003).
Yang, C., et al., "R-ketamine: a Rapid-onset and Sustained Antidepressant Without Psychotomimetic Side Effects," Translational Psychiatry, 5:e632, Nature Publishings Group, United States (Sep. 2015).
Yang, Y., et al., "Ketamine Blocks Bursting in the Lateral Habenula to Rapidly Relieve Depression," Nature, 554(7692):317-322, Basingstoke, Nature Publishing Group (Feb. 2018).
Yao, N., et al., "Ketamine and Its Metabolite (2R,6R)-Hydroxynorketamine Induce Lasting Alterations in Glutamatergic Synaptic Plasticity in the Mesolimbic Circuit," Molecular Psychiatry, 23(10):2066-2077, Houndmills, Nature Publishing Group Specialist Journals (Nov. 2017).
Zanos, P., and Gould, T.D., "Intracellular Signaling Pathways Involved in (S)- and (R)-Ketamine Antidepressant Actions," Biological Psychiatry, 83(1):2-4, Elsevier, United States (Jan. 2018).
Zanos, P., et al., "(2R,6R)-hydroxynorketamine exerts mGlu2 Receptor-dependent Antidepressant Actions," Proceedings of the National Academy of Sciences of the United States of America, 116(13):6441-6450, National Academy of Sciences, United States (Mar. 2019).
Zanos, P., et al., "Ketamine and Ketamine Metabolite Pharmacology: Insights into Therapeutic Mechanisms.," Pharmacological Reviews, 70(3):621-660, American Society for Pharmacology and Experimental Therapeutics, United States (Jul. 2018).
Zangs, P., et al., "Mechanisms of Ketamine Action as an Antidepressant," Molecular Psychiatry, 23(4):801-811, Nature Publishing Group Specialist Journals, England (Apr. 2018).
Zangs, P., et al., "NMDAR Inhibition-Independent Antidepressant Actions of Ketamine Metabolites," Nature, 533:481-486, Basingstoke, Nature Publishing Group (May 2016).
Zangs, P., et al., "(R)-Ketamine Exerts Antidepressant Actions Partly Via Conversion to (2R,6R)-Hydroxynorketamine, While Causing Adverse Effects at Sub-Anesthetic Doses," British Journal of Pharmacology, 44, London, Wiley (Apr. 2019).
Zarate, C.A., et al., "Replication of Ketamine's Antidepressant Efficacy in Bipolar Depression: a Randomized Controlled Add-on Trial," Biological Psychiatry, 71(11):939-946, Elsevier, United States (Jun. 2012).
Zarate, C.A Jr., et al., "A Randomized Trial of an N-methyl-D-Aspartate Antagonist in Treatment-Resistant Major Depression," Archives of General Psychiatry, 63(8):856-64, Chicago, American Medical Assn (Aug. 2006 ).
Zarate, C.A Jr., et al., "Relationship of Ketamine's Plasma Metabolites with Response, Diagnosis, and Side Effects in Major Depression," Biological Psychiatry, 72(4):331-338, New York, Elsevier (Aug. 2012).
Zhang, J.C., et al., "R (−)-ketamine Shows Greater Potency and Longer Lasting Antidepressant Effects Than S (+)-ketamine," Pharmacology, Biochemistry, and Behavior, 116:137-141, Elsevier, United States (Jan. 2014).
Zhang, K., et al., "Essential Roles of Ampa Receptor Glua1 Phosphorylation and Presynaptic Hcn Channels in Fast-acting Antidepressant Responses of Ketamine," Science Signaling, 9(458):ra123, American Association for the Advancement of Science, United States (Dec. 2016).
Zhang, K., et al., "Lack of Metabolism in (R)-Ketamine's Antidepressant Actions in a Chronic Social Defeat Stress Model," Scientific Reports, 8(1):4007, London, Nature Publishing Group (Mar. 2018).
Zhang, M.W., et al., "Analysis of Print News Media Framing of Ketamine Treatment in the United States and Canada From 2000 to 2015," PLoS One, 12(3):e0173202, Public Library of Science, United States (Mar. 2017).
Zhang, M.W., et al., "Analysis of Print News Media Framing of Ketamine Treatment in the United States and Canada From 2000 to 2015," PLoS One, 12(3):e0173202, San Francisco, Public Library of Science (Mar. 2017).
Zhao, X., et al., "Simultaneous Population Pharmacokinetic Modelling of Ketamine and Three Major Metabolites in Patients With Treatment-resistant Bipolar Depression," British Journal of Clinical Pharmacology, 74(2):304-314, Wiley-Blackwell, England (Aug. 2012).
Zheng, W., et al., "Investigation of Medical Effect of Multiple Ketamine Infusions on Patients With Major Depressive Disorder.," Journal of psychopharmacology (Oxford, England), 33(4):494-501, Sage Publications, United States (Apr. 2019).
Harbut, R.E. and Correll, G.E., "Successful Treatment of a Nine-Year Case of Complex Regional Pain Syndrome Type-I (Reflex Sympathetic Dystrophy) With Intravenous Ketamine-Infusion Therapy in a Warfarin-Anticoagulated Adult Female Patient," Pain Medicine, 3(2):147-155, American Academy of Pain Medicine, United States (2002).
Extended European Search Report dated Dec. 11, 2018 in European Patent Application No. 16818548.6, 7 pages.
Office Action dated Mar. 27, 2020 issued in CN Appl. No. 201680037543.8, filed by Shenox Pharmaceuticals, LLC.
English translation of Office Action dated Mar. 27, 2020 issued in CN Appl. No. 201680037543.8, filed by Shenox Pharmaceuticals, LLC.
Office Action dated Apr. 20, 2020 issued in JP Appl. No. 2017-566151, filed by Shenox Pharmaceuticals, LLC.
English translation of Office Action dated Apr. 20, 2020 issued in JP Appl. No. 2017-566151, filed by Shenox Pharmaceuticals, LLC.
Pastore, M.N., et al. "Transdermal patches: history, development and pharmacology," British Journal of Pharmacology 172:2179-2209 (2015), The British Pharmacological Society.
Ruela, A. L. M. et al. "Evaluation of skin absorption of drugs from topical and transdermal formulations" Brazilian Journal of Pharmaceutical Sciences, 52:527-544(2016).
Wilbur R.L. et al. "The difference between topical and transdermal medications," White paper by Gensco Pharma, May 2017, available at https://genscopharma.com/difference-topical-transdermal-medications/ last accessed May 20, 2020.
Ueda C. T. et al. "Topical and Transdermal Drug Products," Pharmacopeial Forum, vol. 35(3), p. 750-764 (2009),The United States Pharmacopeial Convention, Inc.
Leppert W. "Transdermal and Topical Drug Administration in the Treatment of Pain," Molecules 23:681(2018).
Bassani A.S. and Banov, D. "Evaluation of the Percutaneous Absorption of Ketamine HCl, Gabapentin, Clonidine HCl, and Baclofen, in Compounded Transdermal Pain Formulations, Using the FranzFinite

(56) References Cited

OTHER PUBLICATIONS

Dose Model" Pain Medicine, 2015; 00: 00-00, Wiley Periodicals, Inc., Downloaded from https://academic.oup.com/painmedicine/article-abstract/17/2/230/2460674 by guest on Apr. 29, 2020.

* cited by examiner

KETAMINE TRANSDERMAL DELIVERY SYSTEM

CROSS REFERENCE TO RELATED APPLICATIONS

This application claims priority to U.S. provisional patent application No. 62/185,573 filed Jun. 27, 2015.

FIELD OF THE INVENTION

The present invention is directed to transdermal delivery devices comprising ketamine and formulations thereof. The present invention is also directed to transdermal delivery devices comprising ketamine for the treatment of major depressive disorder (MDD) and/or pain. The present invention is further directed to transdermal delivery devices comprising ketamine and abuse deterrent agents.

BACKGROUND OF INVENTION

Major depressive disorder (MDD) is a disabling psychiatric illness. Lifetime prevalence of MDD is approximately 16%. Kessler et al., JAMA, 289(23):3095-105 (2003). There are three primary classes of antidepressants that are commonly prescribed for MDD: (1) monoamine oxidase inhibitors (MAOIs); (2) tricyclics; and (3) serotonin-norepinephrine reuptake inhibitors (SNRIs) and selective serotonin reuptake inhibitors (SSRIs). There are significant limitations with the use of current antidepressants, including limited efficacy, delayed onset of action, and adverse side effects. Additionally, antidepressants have been found to be only about 20-30% more effective than placebo. The delay of onset varies from weeks to months, which may result in adverse events, including but not limited to increased vulnerability to suicide, decrease in compliance, and increase in social and economic burden. Common side effects of these antidepressants include nausea, insomnia, anxiety, weight-loss/gain, drowsiness, headache, loss of sex drive, and/or blurred vision. Penn and Tracey, Ther Adv. Psychopharmacol., 2(5):179-188 (2012).

Pain can present as a disabling physical illness. One type of pain, neuropathic pain, is a complex chronic pain state often accompanied by tissue injury. The occurrence of pain with neuropathic characteristics is about 6.9-10% of the general population. Hecke et al., Pain, 155(4):654-62 (2014). Symptoms of neuropathic pain include spontaneous burning, shooting pain, hyperalgesia, and allodynia. Patients with neuropathic pain often have conditions that are associated with other significant health issues, including depression, sleep problems, and loss of independence. Bouhassira et al., Pain., 136(3):380-7 (2008). Neuropathic pain can be caused by a variety of mechanisms, including infection, central or peripheral nerve injury, stroke, multiple sclerosis, diabetes mellitus, sarcoidosis, toxic agents (e.g., alcohol or chemotherapy), inherited or genetic neuropathy, and Complex Regional Pain Syndrome (CRPS). CRPS is an intractable form of pain, often resistant to a variety of conventional therapies. Correll et al., Pain Med., 5(3):263-75 (2004). Neuropathic pain is difficult to treat, with only about 40-60% of patients achieving partial relief. Treatment for neuropathic pain includes antidepressants, anticonvulsants, and/or topical pain management medications. Niesters et al., Expert Opin. Drug Metab. Toxicol., 8(11):1409-17 (2012); Dworkin et al., Pain, 132(3):237-51 (2007).

Ketamine is a non-competitive, N-methyl-D-aspartate (NMDA) receptor antagonist, indicated for treatment as an anesthetic, sedative, and analgesic. Ketamine has been demonstrated to be an effective antidepressant, with rapid onset (within about 2 hours of administration) and sustained antidepressant effect (from days to in some cases a week or two after administration). Berman et al., Biol. Psychiatry, 47(4):351-54 (2000). The NMDA receptor pathway plays an important role in pain, including neuropathic pain. Animal studies and human clinical studies have shown the efficacy of ketamine in the treatment of chronic neuropathic pain. Correll et al., Pain Med. 5(3):263-75 (2004); Sigtermans et al., Pain, 145(3):304-11 (2009).

Ketamine is a racemic mixture containing R-ketamine and S-ketamine. It is generally believed that the anesthetic and/or antidepressant effect of ketamine is mainly through the action of S-ketamine because in vitro S-ketamine has about a 4-fold greater affinity than the R-ketamine on NMDA receptor binding. However, animal model studies have suggested that R-ketamine is more effective as an antidepressant than S-ketamine. In addition, R-ketamine was shown to be free of psychotomimetic side effects and abuse liability. Yang et al., Transl. Psychiatry, 5(e632):1-11 (2015). The present invention is directed toward administration of the racemic mixture of ketamine; however, embodiments containing the R-ketamine or the S-ketamine enantiomers are within the scope of the present invention.

Ketamine is also a known dissociative anesthetic that has gained popularity as a drug of abuse, and may be referred to illicitly as "K" or "Special K". Ketamine is reported to distort perceptions of sight and sound, and make the user feel disconnected. The 2011 "Monitoring the Future" (MTF) study reports the annual use of ketamine among $8^{th}$, $10^{th}$, and $12^{th}$ graders as being 0.8%, 1.2%, and 1.7%, respectively. Johnston, et al., 2012, Monitoring the future national results on adolescent drug use: Overview of key findings, 2011, Ann Arbor: Institute for Social Research, The University of Michigan. Illicit ketamine can be distributed as a dried powder or as a liquid, mixed with beverages, and/or added to smokable materials (such as marijuana or tobacco). As a powder, ketamine can be snorted or pressed into tablets, sometimes in combination with other drugs, including 3,4-methylenedioxymethamphetamine (MDMA, referred to illicitly as "ecstasy"), amphetamine, methamphetamine, cocaine, and/or carisoprodol. On Aug. 12, 1999 ketamine became a Schedule III non-narcotic substance under the Controlled Substances Act. Consequently, there is a need to develop abuse deterrent mechanisms to reduce the risk of ketamine abuse.

IV administration of ketamine presents numerous challenges. First, the patient incurs increased costs to receive IV administration. Second, IV administration is inconvenient for the patient, and may lead to reduced compliance. Third, the rapid initial rise in ketamine plasma concentrations following IV administration to the maximum plasma concentration ($C_{max}$) can cause adverse side effects, including drug toxicity, psychotomimetic problems, and increased potential for addiction. Moreover, because ketamine has a short half-life (about 2 hours), this immediate release delivery of ketamine by IV administration may result in little to no ketamine remaining in plasma after about 4-8 hours, necessitating frequent and repeated dosing to maintain therapeutic plasma levels. Fourth, without additional safeguards, IV administration of ketamine may be susceptible to abuse.

An intranasal formulation of the S-enantiomer of ketamine, esketamine, is under development and in clinical study by Janssen. US 2013/0236573 A1, Singh et al., Esketamine For The Treatment of Treatment-Refractory Or Treatment-Resistant Depression. However, intranasal delivery of ketamine presents numerous challenges. It suffers from many of the same immediate release issues faced by IV administration of ketamine, namely, rapid onset of maximum concentration ($T_{max}$), high $C_{max}$, increased risk of side effects like drug toxicity, and the need for frequent and multiple dosing to maintain therapeutic plasma concentrations. Frequent administration of intranasal ketamine may increase the risk of irritating and damaging the nasal epithelium, which in turn may reduce patient compliance. Also, intranasal administration is associated with high variability in absorption among subjects. Kublik et al., Adv. Drug Deliv. Rev. 29:157-77 (1998). Further, the rapid rise in ketamine plasma concentration following intranasal administration may cause adverse side effects, such as drug toxicity. Moreover, intranasal delivery of ketamine, without additional safeguards, is highly susceptible to abuse. Other routes of administration of ketamine, including parenteral administration of ketamine (e.g., subcutaneous, intramuscular, etc.) suffer from many of these same challenges.

While oral administration (i.e., tablet or capsule) is typically convenient for the patient, the metabolic and pharmacokinetic properties of ketamine make oral administration less suitable. Ketamine has a high systemic (primarily hepatic) clearance of about 19 ml/min·kg, a rate which approaches liver plasma flow. Thus, ketamine is subject to substantial pre-systemic metabolism, or first-pass effect, in the liver and gut wall by metabolic enzymes, such as cytochrome P450 enzymes (CYP450). Consequently, the absolute oral bioavailability of ketamine in humans is only about 10-20%. Due to this first-pass effect, there is an increased risk for drug-drug interactions (DDI) with drugs that can inhibit or induce CYP450s. Clements et al., J Pharm Sci, 71(5):539-42 (1981); Fanta, et al., Eur. J. Clin. Pharmacol., 71:441-47 (2015); Peltoniemi et al., Basic & Clinical Pharmacology & Toxicology, 111:325-332 (2012). Moreover, ketamine tablets or capsules are easily abused.

SUMMARY OF THE INVENTION

The present invention is directed to transdermal delivery devices comprising ketamine and formulations thereof. The present invention is also directed to transdermal delivery devices comprising ketamine for the treatment of major depressive disorder (MDD) and/or pain. There are long-felt and unmet medical needs for the treatment of MDD and for the treatment of pain, which are fulfilled by the present invention. The controlled, prolonged, and steady ketamine exposure to humans from the transdermal delivery device of the present invention can reduce adverse side effects compared with other routes of ketamine delivery, including but not limited to intravenous (IV) administration and intranasal spray. Because ketamine has high abuse potential, the present invention is further directed to transdermal delivery devices comprising ketamine and abuse deterrent agents.

The present invention has numerous advantages. Formulations of the transdermal delivery device provide excellent ketamine permeability and stability. The inventors discovered, through in vitro experiments, that ketamine has excellent transdermal permeability properties, which are very important for efficacious clinical use. Additional in vitro experiments demonstrated that adding, for example, crystallization inhibitors to formulations of the present invention resulted in very stable transdermal delivery devices, which is important when making a pharmaceutical product.

Additionally, the present invention provides improved drug metabolism and pharmacokinetic properties compared with other methods of administering ketamine, such as IV and intranasal administration. First, transdermal delivery avoids the aforementioned first-pass effect. Second, it reduces the aforementioned DDI risk. Third, it delivers a sustained in vitro release profile, and therefore, a steadier in vivo plasma concentration versus time profile over a longer period of time. In other words, there is no need for frequent, multiple dosing for days or weeks to maintain therapeutic plasma concentrations of ketamine, as may be the case with, for example, IV infusion. Correll et al., Pain Med. 5(3):263-75 (September 2004). Instead, the present invention can meet the desired prolonged drug absorption profile. For example, administration of a single transdermal delivery device of the present invention can deliver a relatively constant ketamine plasma concentration for up to about 7 days. Fourth, the present invention delivers lower $C_{max}$ values for ketamine in the plasma, as well as minimal fluctuation between $C_{max}$ and $C_{min}$, thereby reducing adverse side effects, including but not limited to toxicity, psychotropic effects, increased potential for addiction, and lack of therapeutic effect.

The transdermal delivery device of the present invention provides flexibility in dose, dosage release rate, patch size, and duration of application to allow for optimization. Transdermal delivery devices according to the present invention include, but are not limited to, transdermals and dermal patches, topical skin applications such as spray, creams, gels, lotions, dressings and liquid solutions, and other transdermal delivery systems and dosage forms known to persons skilled in the art. For example, these flexible parameters can be adjusted by the formulator and/or the clinician to provide the optimal ketamine plasma concentration-time profile for the individual patient that maximizes efficacy and minimizes adverse side effects. Therefore, the ketamine transdermal delivery device of the present invention is particularly effective for the treatment of MDD and pain.

Moreover, the present invention improves convenience and compliance compared with other forms of administering ketamine. For example, administration of the transdermal delivery device once or twice a week is more convenient than, for example, multiple daily doses of immediate release forms of ketamine. Immediate release ketamine or immediate release ketamine formulation means administration of ketamine that is not extended, controlled, delayed or prolonged. Dose equivalent with means that the total dosage of drug administered between the compared items is the same. Also, the present invention is less invasive and less costly than IV administration. The present invention causes less irritation and is less invasive than intranasal administration. Further, the present invention is less likely to cause drug toxicity than immediate release forms of drug delivery.

The present invention also has advantages with respect to abuse deterrence. The transdermal delivery device itself may serve as an abuse deterrent because it is more difficult to abuse directly, such as by biting or swallowing the device. Specifically, the ketamine is incorporated into a polymeric matrix together with other excipients, including, but not limited to skin permeation enhancers, humectants, plasticizers, buffers, antioxidants, and combinations thereof, each of which may inhibit ketamine extraction for abuse. Nevertheless, specific, additional abuse deterrent agents can be added to formulations of the present invention to further deter abuse.

DETAILED DESCRIPTION OF THE INVENTION

Figure 1:
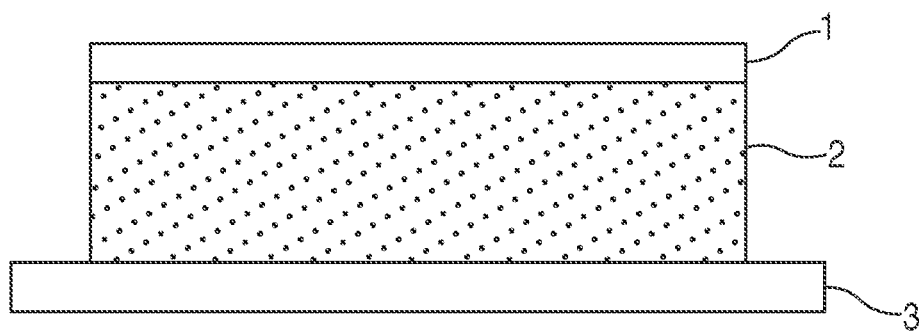
FIG. 1 is a ketamine transdermal delivery device without abuse deterrent properties.

The active ingredient in the transdermal delivery device of the present invention is preferably employed at about 1-35% by weight of the final formulation (also referred to as 1-35 weight percent) and most preferably 10-25% by weight of the final formulation. The most preferred active ingredient is ketamine. Additional active ingredients that can be employed in the present invention can be chosen from drugs that counteract the potential adverse effects of ketamine, reduce ketamine addiction potential, and/or enhance ketamine's antidepressant effect and/or pain management effects. All weight percentages provided in the present disclosure are based on the weight of the final formulation, which includes the adhesive-drug layer (or adhesive-drug matrix) and the abuse deterrent layer (or abuse deterrent matrix, which is optional), but not the release liner or the backing film.

The transdermal permeation rate (mg/day) combined with the size of the transdermal delivery device and the duration of application of the transdermal delivery device determines the plasma concentration of the drug. The transdermal permeation rate of the ketamine transdermal delivery device of the present invention will preferably be about 0.1-30 mg/day/cm$^2$ of the transdermal delivery device, and most preferably about 0.5-5 mg/day/cm$^2$. The size of transdermal delivery device will preferably be about 5-300 cm$^2$. The duration of application of the transdermal devices will preferably be about 8-168 hours. Combinations of these preferred ranges provide prolonged plasma concentrations of ketamine ranging from about 0.4-3850 ng/ml. The plasma concentrations of ketamine will reach near steady-state at about 8 hours after administration and will be sustained for the duration of the application.

Preferred transdermal permeation rates, transdermal delivery device sizes, and durations of applications for the transdermal delivery devices of the present invention are set forth in Table 1.

TABLE 1

| Permeation rates (mg/day/cm$^2$) | Transdermal delivery device size (cm$^2$) | Application Duration (days) | Dosage strength (mg) | Plasma concentrations after about 8 hours (ng/ml) |
| --- | --- | --- | --- | --- |
| 0.1-30 | 10 | 1/3 | 0.33-100 | 0.43-128 |
| 0.1-30 | 300 | 1/3 | 10-3000 | 13-3850 |
| 0.1-30 | 10 | 1 | 1-300 | 0.43-128 |
| 0.1-30 | 300 | 1 | 30-9000 | 13-3850 |
| 0.1-30 | 10 | 7 | 7-2100 | 0.43-128 |
| 0.1-30 | 300 | 7 | 210-63000 | 13-3850 |

The plasma concentrations of ketamine versus time are calculated based on the reported pharmacokinetic parameters of ketamine in humans. Ketamine follows a three-compartment model with the parameters for a 70-kg human as follows: clearance=79.8 (liter/hour); V1=133 liter; and micro constants $k_{12}$=0.174 hour$^{-1}$, $k_{13}$=1.18 hour$^{-1}$, $k_{21}$=0.124 hour$^{-1}$, $k_{31}$=1.59 hour$^{-1}$. Fanta, et al., Eur. J. Clin. Pharmacol., 71:441-447 (2015). There is variability among human populations and individuals, such that the pharmacokinetics of each human are not the same, and for certain populations and for some individuals, the pharmacokinetics can deviate significantly. Plasma concentrations provided by any given dosage strength for the transdermal delivery device of the present invention can vary from individual to individual.

For antidepressant effect (i.e., the treatment of MDD) with minimized adverse side effects, the preferred plasma concentration range of ketamine is from about 10-200 ng/ml, and the most preferred plasma concentration range is from about 10-100 ng/ml.

Table 2 provides ranges for the most preferred transdermal permeation rates, transdermal delivery device sizes, and duration of application of the transdermal delivery devices for antidepressant effect (i.e., the treatment of MDD) with minimized adverse side effects. These ranges are chosen to provide prolonged plasma concentrations of ketamine ranging from about 10-200 ng/ml for about 8-168 hours, and the most preferred plasma concentrations are from about 10-100 ng/ml. Variations on the transdermal delivery devices comprising ketamine designed for the treatment of MDD will contain from about 8.3-200 mg and be applied for about 8 hours, from about 25-600 mg and be applied for about 24 hours, from about 87.5-2100 mg and be applied for about 84 hours, and from about 175-4200 mg and be applied for about 168 hours.

Transdermal delivery devices for the treatment of MDD are prepared with dosage strengths from about 8.3-200 mg, and are designed to be applied for about 8 hours, which will provide a plasma concentration of ketamine from about 11-257 ng/ml. An alternate embodiment of the present invention for the treatment of MDD is designed to provide reduced adverse side effects. The reduced adverse side effects are provided by a transdermal delivery device according to the present invention prepared with dosage strengths of ketamine from about 8.3-100 mg of ketamine, designed to be applied for 8 hours, and to provide a plasma concentration of ketamine from about 11-128 ng/ml.

Transdermal delivery devices for the treatment of MDD according to the present invention are prepared with dosage strengths from about 25-600 mg and are designed to be applied for about 24 hours, which will provide a plasma concentration of ketamine from about 11-257 ng/ml. An alternate embodiment of the present invention for the treatment of MDD is designed to provide reduced adverse side effects. The reduced adverse side effects are provided by a transdermal delivery device according to the present invention prepared with dosage strengths of ketamine from about 25-300 mg of ketamine, designed to be applied for 24 hours, and to provide a plasma concentration of ketamine from about 11-128 ng/ml.

Transdermal delivery devices for the treatment of MDD according to the present invention are prepared with dosage strengths from about 87.5-2100 mg, and are designed to be applied for about 84 hours, which will provide a plasma concentration of ketamine from about 11-257 ng/ml. An alternate embodiment of the present invention for the treatment of MDD is designed to provide reduced adverse side effects. The reduced adverse side effects are provided by a transdermal delivery device according to the present invention prepared with dosage strengths of ketamine from about 87.5-1050 mg, designed to be applied for about 84 hours, and to provide a plasma concentration of ketamine from about 11-128 ng/ml.

Transdermal delivery devices for the treatment of MDD according to the present invention are prepared with dosage strengths from about 175-4200 mg, and are designed to be applied for about 168 hours, which will provide a plasma concentration of ketamine from about 11-257 ng/ml. An alternate embodiment of the present invention for the treatment of MDD is designed to provide reduced adverse side effects. The reduced adverse side effects are provided by a transdermal delivery device according to the present invention prepared with dosage strengths of ketamine from about 175-2100 mg, designed to be applied for about 168 hours, and to provide a plasma concentration of ketamine from about 11-128 ng/ml.

TABLE 2

| Permeation rates (mg/day/cm$^2$) | Transdermal delivery device size (cm$^2$) | Application Duration (days) | Dosage strength (mg) | Plasma concentrations after about 8 hours (ng/ml) |
|---|---|---|---|---|
| 1 | 25-300 | 1/3 | 8.3-100 | 11-128 |
| 5 | 5-60 | 1/3 | 8.3-100 | 11-128 |
| 5 | 5-120 | 1/3 | 8.3-200 | 11-257 |
| 1 | 25-300 | 1 | 25-300 | 11-128 |
| 5 | 5-60 | 1 | 25-300 | 11-128 |
| 5 | 5-120 | 1 | 25-600 | 11-257 |
| 1 | 25-300 | 3.5 | 87.5-1050 | 11-128 |
| 5 | 5-60 | 3.5 | 87.5-1050 | 11-128 |
| 5 | 5-120 | 3.5 | 87.5-2100 | 11-257 |
| 1 | 25-300 | 7 | 175-2100 | 11-128 |
| 5 | 5-60 | 7 | 175-2100 | 11-128 |
| 5 | 5-120 | 7 | 175-4200 | 11-257 |

For pain management, with minimized adverse events, the preferred plasma concentrations ranges of ketamine are from about 50-1000 ng/ml, and the most preferred plasma concentration is about 500 ng/ml.

Table 3 provides ranges for transdermal permeation rates, transdermal delivery device sizes, and duration of application of the transdermal delivery devices for pain management. These ranges are chosen to provide prolonged plasma concentrations of ketamine ranging from about 50-1000 ng/ml, and for about 8-168 hour, and the most preferred plasma concentration is about 500 ng/ml. Transdermal delivery devices comprising ketamine designed for pain management will contain about 40-500 mg and be applied for about 8 hours, from about 120-1500 mg and be applied for about 24 hours, from about 420-5250 mg and be applied for about 84 hours, and from about 840-10500 mg and be applied for about 168 hours.

Transdermal delivery devices for the treatment of pain according to the present invention are prepared with dosage strengths from about 40-500 mg, are designed to be applied for about 8 hours, and will provide a plasma concentration of ketamine from about 51-642 ng/ml.

Transdermal delivery devices for the treatment of pain according to the present invention are prepared with dosage strengths from about 120-1500 mg, are designed to be applied for about 24 hours, and will provide a plasma concentration of ketamine from about 51-642 ng/ml.

Transdermal delivery devices for the treatment of pain according to the present invention are prepared with dosage strengths from about 420-5250 mg, are designed to be applied for about 84 hours, and will provide a plasma concentration of ketamine from about 51-642 ng/ml.

Transdermal delivery devices for the treatment of pain according to the present invention are prepared with dosage strengths from about 840-10,500 mg, are designed to be applied for about 168 hours, and will provide a plasma concentration of ketamine from about 51-642 ng/ml.

TABLE 3

| Permeation rates (mg/day/cm$^2$) | Transdermal delivery device Size (cm$^2$) | Application Duration (day) | Dosage strength | Plasma concentrations after about 8 hours (ng/ml) |
|---|---|---|---|---|
| 1 | 120-300 | 1/3 | 40-100 | 51-128 |
| 5 | 24-300 | 1/3 | 40-500 | 51-642 |
| 1 | 120-300 | 1 | 120-300 | 51-128 |
| 5 | 24-300 | 1 | 120-1500 | 51-642 |
| 1 | 120-300 | 3.5 | 420-1050 | 51-128 |
| 5 | 24-300 | 3.5 | 420-5250 | 51-642 |
| 1 | 120-300 | 7 | 840-2100 | 51-128 |
| 5 | 24-300 | 7 | 840-10500 | 51-642 |

Preferably, the transdermal delivery device of the present invention will be administered once a day, twice a week, or once a week. The dosing regimen of the present invention is not limited to the examples provided in Tables 2 and 3 for antidepressant effect and pain management. In accordance with the need of the patient and as determined by the physician, the dose frequencies, device size, and/or dosage strength can be adjusted. For example, the application of the transdermal delivery device can be for a duration shorter than 8 hours, such as 4 hours. The ketamine plasma concentrations at about 4 hours after administration will be about 80% of the plasma concentration at about 8 hours, which can provide effective anti-depressant and/or pain management, depending on the need of the patient.

Figure 5:
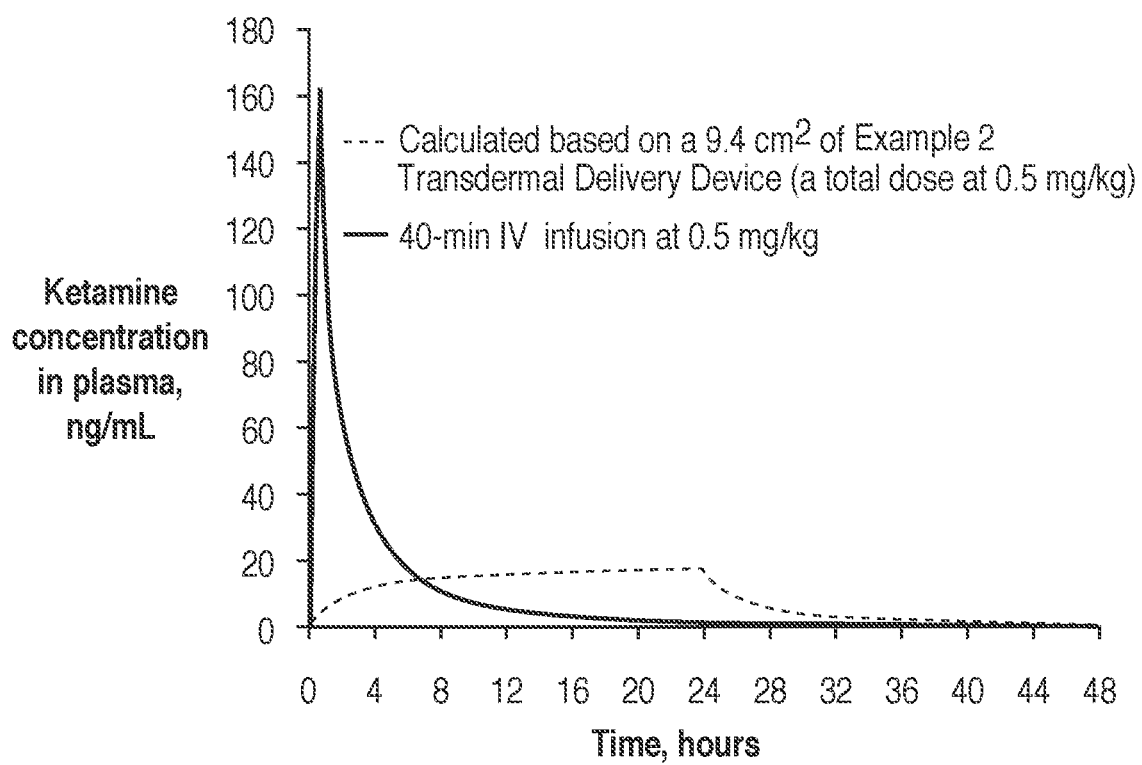
FIGS. 5-7 are ketamine plasma concentration versus time profiles in humans for Example 2 of the present invention using different sizes of the transdermal delivery device. These pharmacokinetic profiles are predicted by known convolution methodology using in vitro transdermal permeation data and in vivo intravenous plasma concentration data.
Figure 6:
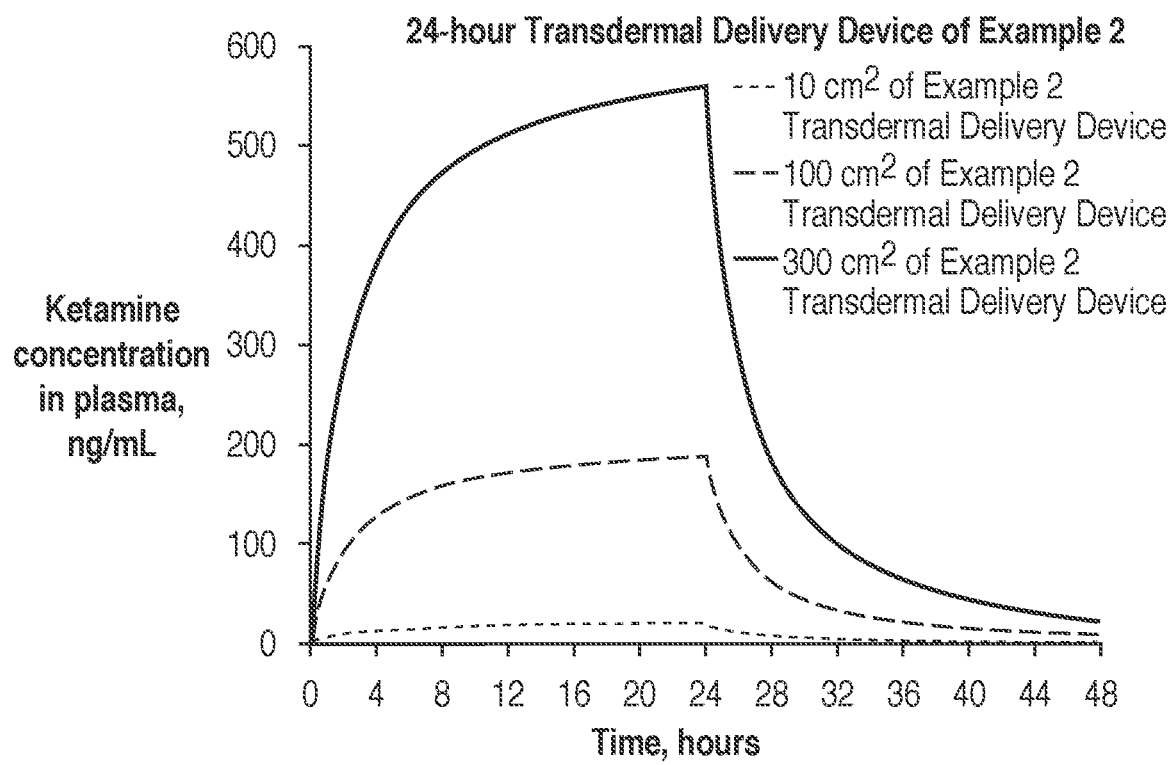
Figure 7:
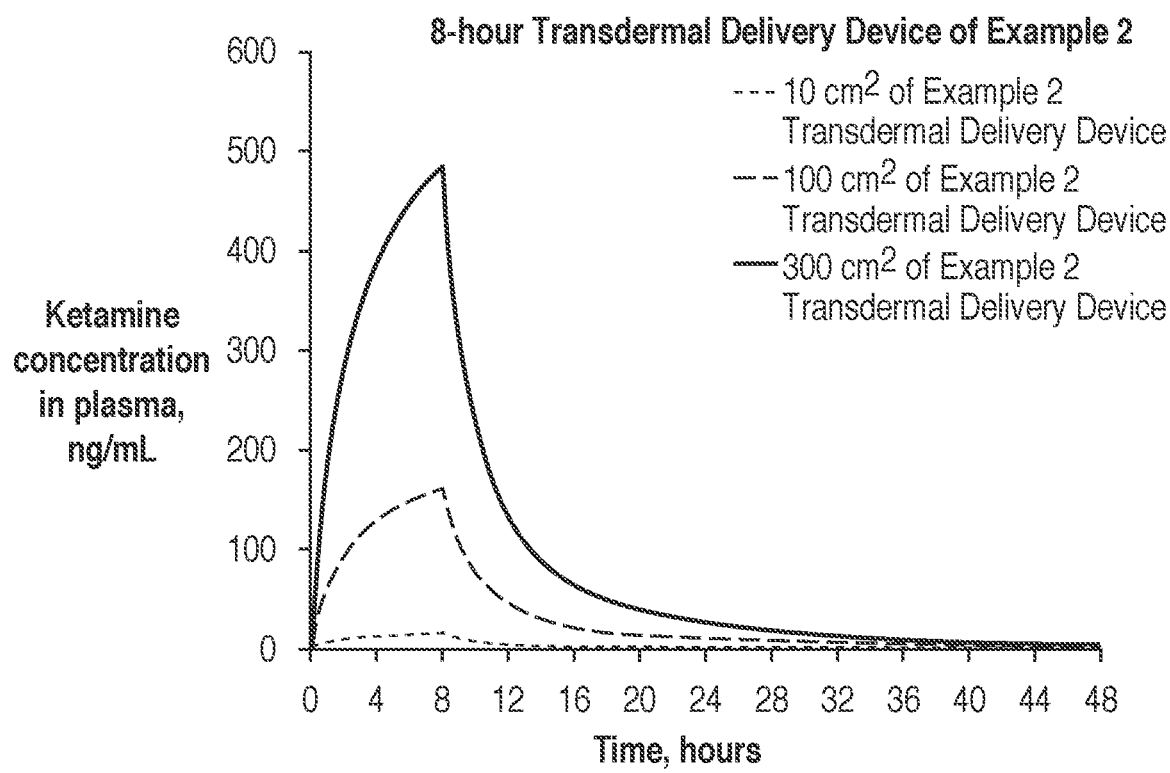

The plasma drug concentrations profiles in Table 4 and illustrated in FIGS. 6-7, are exemplary of the plasma profiles of the present invention. The plasma drug concentration profiles in Tables 2 and 3 and illustrated at least in 10-17, are further exemplary of the plasma profiles of the present invention. These plasma profiles rise slowly and are maintained at a relatively constant level for a prolonged period of time. On the contrary, IV and intranasal ketamine will generally provide a $C_{max}$ approximately 3 to 10 times higher than the $C_{max}$ provided by a transdermal delivery device of the present invention (at equivalent doses), while the area under the curve (AUC) is constant (e.g., FIG. 5). Additionally, the prolonged and steady administration of ketamine provided by the transdermal delivery device of the present invention exhibits minimal fluctuations in plasma concentration relative to multiple doses of IV or intranasal administration of ketamine. This reduction or minimization of plasma fluctuations in turn reduces the occurrence of adverse side effects resulting from under and over medication. Consequently, the plasma profile provided by the present invention is improved and may result in better therapeutic outcomes and greater patient compliance.

The structure and packaging of the transdermal delivery device of the present invention are prepared in accordance with methods and techniques known to persons skilled in the art. The primary components are the backing layer, the adhesive-drug layer (or adhesive-drug matrix), the abuse deterrent layer (or abuse deterrent matrix) (optional), and the release liner.

The backing layer may be comprised of polymeric films such as polyester (PET) or polyethylene (PE) films that support the adhesive drug matrix and protect the transdermal delivery device from the environment. The preferred thickness range for the backing film is from about 2-5 mils (1 mil equals 1/1000 of an inch), and the most preferred thickness range of the backing layer is from about 3-4 mils thick.

The adhesive in the adhesive-drug layer may be a pressure sensitive adhesive (PSA). Tan et al., *Pharm Sci. & Tech Today*, 2:60-69 (1999). Useful PSAs in transdermal delivery systems include, but are not limited to, polyisobutylenes (PIB), silicone polymers, and acrylate copolymers, such as acrylic pressure sensitive adhesives, including Duro-Tak 87-2516, 87-2852 and 87-2194, manufactured by Henkel Adhesives. PIBs are elastomeric polymers that are commonly used in PSAs, both as primary-base polymers and as tackifiers. PIBs are homopolymers of isobutylene and feature a regular structure of a carbon-hydrogen backbone with only terminal unsaturation. PIBs are marketed under the trade name Oppanol by BASF. The silicone polymers are a high molecular weight polydimethylsiloxane that contains residual silanol functionality (SiOH) on the ends of the polymer chains. Silicone PSAs for use in pharmaceutical applications are available from Dow Corning Corporation, for example under the trade name of BIO-PSA. The PSA is preferably employed at about 30-90% by weight of the final formulation, and most preferably about 40-60% by weight of the final formulation.

The release liner can be manufactured in the desired size for the present invention. The release liner may be comprised of silicone or fluoro-polymer coated polyester film. The release liner protects the transdermal delivery device during storage and is removed before its use. Silicone-coated release liners are manufactured by Mylan Corporation, Loparex Corporation, and 3M's Drug Delivery Systems. The fluoro-polymer coated release liners are manufactured and supplied by 3M's Drug Delivery Systems and Loparex. The preferred thickness of the release liner is about 2-10 mils, and most preferably about 3-5 mils.

Additional drugs can be incorporated in the transdermal delivery device to counteract adverse effects, and/or to enhance the antidepressant or pain management effect of ketamine. Examples for enhancing antidepressant effect include, but are not limited to, antagonists of group II metabotropic glutamate receptors, such as LY341495, Podkowa et al., Psychopharmacology (Berl) (Jun. 11, 2016). Examples for reducing side effects with ketamine, especially psychotomimetic and sympathomimetic, include, but not limited to, co-administration of alpha-2 agonists such as clonidine. Lenze, World J Biol Psychiatry, 17(3):230-8 (2016). If an additional drug is employed in the present invention, it is preferably employed at about 0.1-20% by weight of the final formulation, and most preferably about 1-5% by weight of the final formulation.

Additional components can be added to the transdermal delivery device of the present invention to optimize it. Skin permeation enhancers are employed to enhance the skin permeability of the drug through the skin. Skin permeation enhancers that may be employed in the present invention include, but are not limited to, sulphoxides (e.g. dimethylsulphoxide, DMSO), Azones (e.g. laurocapram), pyrrolidones (e.g. 2-pyrrolidone, 2P), alcohols and alkanols (ethanol, or decanol), glycols (e.g. propylene glycol (PG)), surfactants and terpenes. Williams et al., Adv Drug Deliv Rev. 27; 56(5):603-18 (2004). The skin permeation enhancers are preferably employed at about 1-20% by weight of the final formulation, and most preferably about 4-10% by weight of the final formulation.

Humectants are employed to keep the transdermal delivery device hydrated and/or to reduce the loss of moisture. The humectants that may be employed in the present invention include, but are not limited to, propylene glycol, glycerol, urea, polyvinylpyrrolidone (PVP), vinylpyrrolidone-vinyl acetate copolymers, and copolymers of PVP (e.g., BASF's Kollidon K30, K12, Kollidon VA 64, or Kollidon CL-M, magnesium silicate, and silica. The humectants are preferably employed at about 2-20% by weight of the final formulation and most preferably about 5-10% by weight of the final formulation.

Plasticizers are employed in transdermal drug delivery systems to obtain desirable mechanical properties, such as to improve the film forming properties and the appearance of the film, to decrease the glass transition temperature of the polymer, to prevent film cracking, and to increase film flexibility. The plasticizers that may be employed in the present invention include, but are not limited to, phthalate esters, phosphate esters, fatty acid esters, and glycol derivatives. The plasticizers are preferably employed at about 2-20% by weight of the final formulation and most preferably about 5-10% by weight of the final formulation. Designing and Characterization of Drug Free Transdermal delivery devices for Transdermal Application, International Journal of Pharmaceutical Sciences and Drug Research, Vol. 2, No. 1, pp. 35-39 Bharkatiya, M.; Nema, R. K. & Bhatnagar, M. (2010) Wypch, G. (2004) and Handbook of Plasticizers, Chem Tec, 437-440, ISBN 1-895198-29-1, Ontario, Canada.

Antioxidants are employed to prevent drug degradation by oxidation. Antioxidants that may be employed in the present invention include, but are not limited to, butylated hydroxyanisole (BHA), butylhydroxy toluene (BHT), tert-Butylhydroquinone, ascorbic acid, and tocopherols. The antioxidants are preferably employed at about 0.01-5% by weight of the final formulation and most preferably about 0.1-1.0% by weight of the final formulation.

Anti-irritants are employed to provide alleviation or prevention of skin irritation, and to assist in the release of the active ingredients. Anti-irritants that may be employed in the present invention include, but are not limited to, aloe, *arnica*, chamomile, cucumber, menthol, mugwort, oat, zinc oxide, drug release modifiers such as chitosan, cellulose-based polymers, silicon dioxides, and polymethacrylates.

Other suitable excipients useful in the preparation of transdermal delivery devices are within the knowledge of those skilled in the art, and can be found in the Handbook of Pharmaceutical Excipients, (7th ed. 2012), the entire content of which is hereby incorporated by reference.

FIG. 1 is an embodiment of the transdermal delivery device in which the backing film (1) is affixed atop the adhesive drug matrix (2), which is supported by a release liner (3). The adhesive drug matrix contains the drug and adhesive, as well as enhancers, humectants, plasticizers, antioxidants, pH modifiers, crystallization inhibitors, and other ingredients that aid in drug release and permeation through skin, and in maintaining drug stability.

Figure 2:
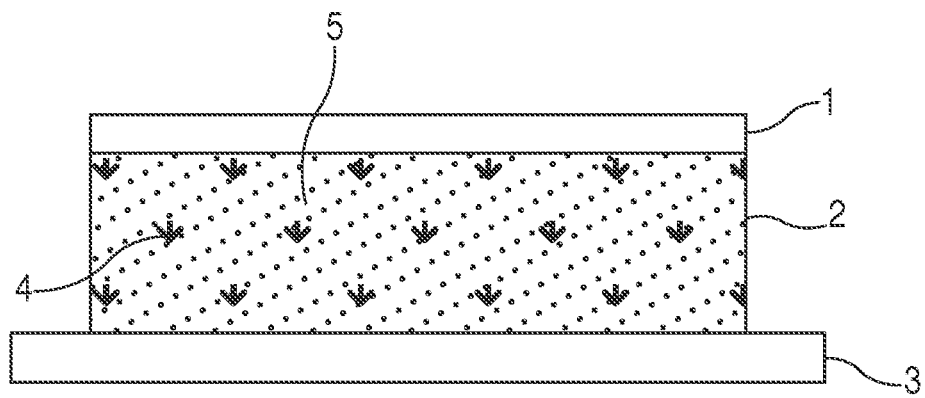
FIG. 2 is a transdermal delivery device comprising ketamine with abuse deterrent properties.

FIG. 2 is an example of a transdermal delivery device that contains an abuse deterrent agent (4) that is not skin permeable, drug (5) dissolved in the adhesive-drug matrix (2), a transdermal delivery device backing film (1), and a release liner (3).

Figure 3:
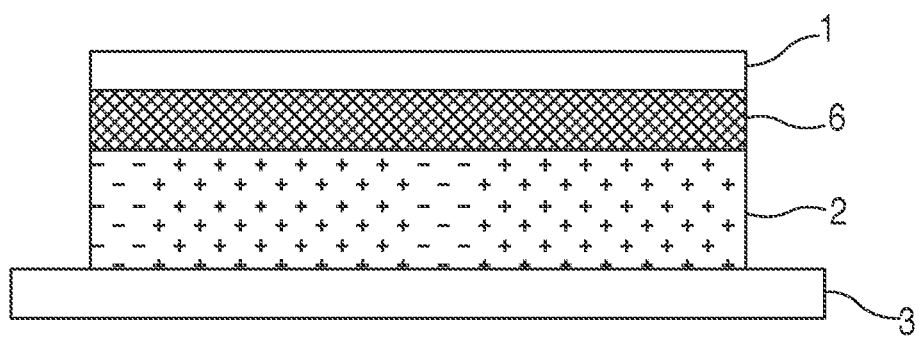
FIG. 3 is an alternate embodiment of a transdermal delivery device comprising ketamine and abuse deterrent agents.

FIG. 3 is a transdermal delivery device that contains a backing film (1), an abuse deterrent layer (6), an adhesive-drug matrix (2), and a release liner (3). The abuse deterrent layer is capable of releasing an abuse deterrent agent upon tampering with the transdermal delivery device. In an embodiment in which the abuse deterrent layer comprises a gel forming agent, the gel forming agent can form a gel solution upon extraction.

Figure 4:
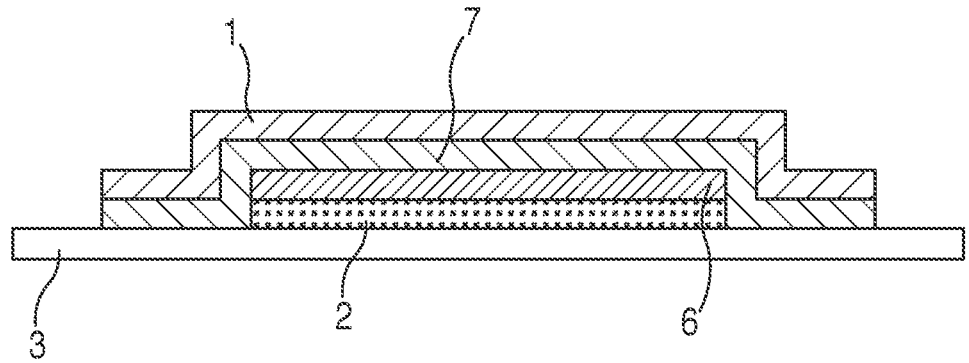
FIG. 4 is an alternate embodiment of a transdermal delivery device comprising ketamine and abuse deterrent agents.

FIG. 4 is an embodiment of a prolonged use, e.g., 7-day transdermal delivery device, with abuse deterrent agents in a segregated, abuse deterrent layer. FIG. 4 shows the backing film (1), and overlay adhesive layer (7), an abuse deterrent layer (6), the adhesive-drug layer (2), and a release liner (3). The overlay adhesive layer extends over the outer edges of the drug-adhesive layer (2) and the abuse deterrent layer (6) to provide added adhesion to the skin for prolonged use. Embodiments of the present invention can be prepared with an overlay adhesive layer (7) with or without an intervening abuse deterrent layer (6).

Table 4 provides estimated plasma concentrations for transdermal delivery devices prepared according to the present invention. The plasma concentration are exemplified in FIGS. 5, 6 and 7, which are described below in detail.

TABLE 4

| Time (hr) | FIG., 5 IV after 24-hr (ng/ml) | | FIG., 6 24-hr Device (ng/ml) | | | FIG., 7 8-hr Device (ng/ml) | | |
|---|---|---|---|---|---|---|---|---|
| | IV (0.5 mg/kg) | 9.4-cm$^2$, 24-hr (0.5 mg/kg) | 10-cm$^2$ | 100-cm$^2$ | 300-cm$^2$ | 10-cm$^2$ | 100-cm$^2$ | 300-cm$^2$ |
| 0 | 0 | 0 | 0 | 0 | 0 | 0 | 0 | 0 |
| 1 | 110 | 5.8 | 6.2 | 62 | 186 | 6.2 | 62 | 186 |
| 2 | 62 | 8.7 | 9.2 | 92 | 276 | 9.2 | 92 | 276 |
| 3 | 43 | 11 | 11 | 113 | 338 | 11 | 113 | 338 |
| 4 | 31 | 12 | 13 | 127 | 382 | 13 | 127 | 382 |
| 5 | 23 | 13 | 14 | 138 | 414 | 14 | 138 | 414 |
| 6 | 17 | 14 | 15 | 146 | 439 | 15 | 146 | 439 |
| 7 | 14 | 14 | 15 | 153 | 458 | 15 | 153 | 458 |
| 8 | 11 | 15 | 16 | 158 | 473 | 16 | 158 | 473 |
| 9 | 8.9 | 15 | 16 | 162 | 485 | 10 | 102 | 305 |
| 10 | 7.4 | 16 | 17 | 165 | 495 | 7.5 | 75 | 223 |
| 11 | 6.4 | 16 | 17 | 168 | 504 | 5.7 | 57 | 169 |
| 12 | 5.5 | 16 | 17 | 170 | 511 | 4.4 | 44 | 132 |
| 13 | 4.9 | 16 | 17 | 173 | 518 | 3.5 | 35 | 106 |
| 14 | 4.3 | 16 | 17 | 175 | 524 | 2.9 | 29 | 87 |
| 15 | 3.9 | 17 | 18 | 176 | 529 | 2.4 | 24 | 73 |
| 16 | 3.5 | 17 | 18 | 178 | 534 | 2.1 | 21 | 63 |
| 17 | 3.2 | 17 | 18 | 179 | 538 | 1.8 | 18 | 54 |
| 18 | 2.9 | 17 | 18 | 181 | 542 | 1.6 | 16 | 48 |
| 19 | 2.6 | 17 | 18 | 182 | 546 | 1.4 | 14 | 43 |
| 20 | 2.4 | 17 | 18 | 183 | 549 | 1.3 | 13 | 38 |
| 21 | 2.2 | 17 | 18 | 184 | 552 | 1.2 | 12 | 35 |
| 22 | 2.0 | 17 | 18 | 185 | 554 | 1.0 | 10 | 31 |
| 23 | 1.8 | 17 | 19 | 186 | 557 | 0.95 | 9.5 | 28 |
| 24 | 1.7 | 18 | 19 | 186 | 559 | 0.86 | 8.6 | 26 |
| 25 | 1.5 | 12 | 13 | 125 | 375 | 0.79 | 7.9 | 24 |
| 26 | 1.4 | 9.0 | 9.6 | 96 | 287 | 0.72 | 7.2 | 21 |
| 27 | 1.3 | 7.1 | 7.6 | 76 | 227 | 0.65 | 6.5 | 20 |
| 28 | 1.2 | 5.8 | 6.1 | 61 | 184 | 0.60 | 6.0 | 18 |
| 29 | 1.1 | 4.8 | 5.1 | 51 | 154 | 0.55 | 5.5 | 16 |
| 30 | 0.97 | 4.1 | 4.3 | 43 | 130 | 0.50 | 5.0 | 15 |
| 31 | 0.88 | 3.5 | 3.8 | 38 | 113 | 0.46 | 4.6 | 14 |
| 32 | 0.81 | 3.1 | 3.3 | 33 | 99 | 0.42 | 4.2 | 13 |
| 33 | 0.74 | 2.7 | 2.9 | 29 | 88 | 0.38 | 3.8 | 11 |
| 34 | 0.68 | 2.5 | 2.6 | 26 | 78 | 0.35 | 3.5 | 10 |
| 35 | 0.62 | 2.2 | 2.3 | 23 | 70 | 0.32 | 3.2 | 9.6 |
| 36 | 0.57 | 2.0 | 2.1 | 21 | 64 | 0.29 | 2.9 | 8.8 |
| 37 | 0.52 | 1.8 | 1.9 | 19 | 58 | 0.27 | 2.7 | 8.0 |
| 38 | 0.47 | 1.6 | 1.7 | 17 | 52 | 0.24 | 2.4 | 7.3 |
| 39 | 0.43 | 1.5 | 1.6 | 16 | 48 | 0.22 | 2.2 | 6.7 |
| 40 | 0.40 | 1.4 | 1.5 | 15 | 44 | 0.21 | 2.1 | 6.1 |
| 41 | 0.36 | 1.2 | 1.3 | 13 | 40 | 0.19 | 1.9 | 5.6 |
| 42 | 0.33 | 1.1 | 1.2 | 12 | 36 | 0.17 | 1.7 | 5.1 |
| 43 | 0.30 | 1.0 | 1.1 | 11 | 33 | 0.16 | 1.6 | 4.7 |
| 44 | 0.28 | 0.95 | 1.0 | 10 | 30 | 0.14 | 1.4 | 4.3 |
| 45 | 0.25 | 0.87 | 0.92 | 9.2 | 28 | 0.13 | 1.3 | 3.9 |
| 46 | 0.23 | 0.79 | 0.85 | 8.5 | 25 | 0.12 | 1.2 | 3.6 |

TABLE 4-continued

| | FIG., 5 IV after 24-hr (ng/ml) | | FIG., 6 24-hr Device (ng/ml) | | | FIG., 7 8-hr Device (ng/ml) | | |
|---|---|---|---|---|---|---|---|---|
| Time (hr) | IV (0.5 mg/kg) | 9.4-cm², 24-hr (0.5 mg/kg) | 10-cm² | 100-cm² | 300-cm² | 10-cm² | 100-cm² | 300-cm² |
| 47 | 0.21 | 0.73 | 0.77 | 7.7 | 23 | 0.11 | 1.1 | 3.3 |
| 48 | 0.19 | 0.66 | 0.71 | 7.1 | 21 | 0.10 | 1.0 | 3.0 |

Figure 8:
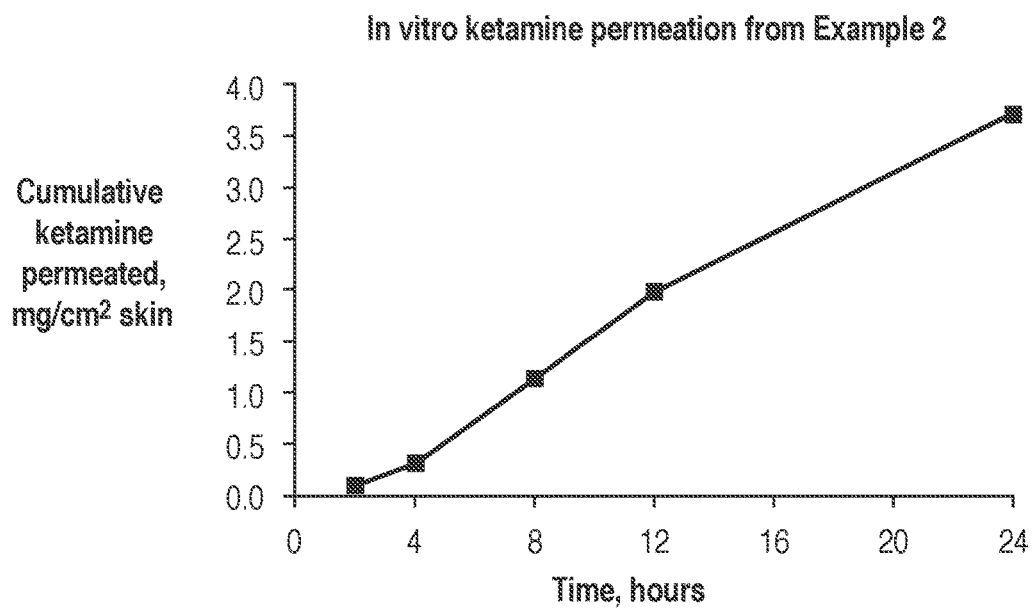
FIG. 8 is a graph of the in vitro skin permeation of ketamine in a Franz Diffusion Cell model for the transdermal delivery device according to Example 2.

Table 5 provides the cumulative amount of ketamine that permeates human skin in the Franz Diffusion Cell model disclosed in FIG. 8, as provided by a transdermal delivery device according to Example 2 of the present invention. The total amount of drug in the transdermal delivery device of Example 2 is 4.75 mg. Therefore, the transdermal bioavailability of Example 2 within 24 hours is about 78%.

TABLE 5

| Time (hr) | Cumulative ketamine permeated (mg/cm²) |
|---|---|
| 2 | 0.0976 |
| 4 | 0.307 |
| 8 | 1.13 |
| 12 | 1.98 |
| 24 | 3.72 |

Transdermal delivery devices can be abused. One method of abuse is to place the device in a solvent to separate the drug from the polymeric matrix, followed by separating the drug from any additional components. In order to deter abuse, the present invention is further directed towards a novel transdermal delivery device comprising ketamine and abuse deterrent agents.

Abuse deterrent agents are employed because they have one or more of the following properties: (1) unpalatable bitterness or other repulsive tastes in the mouth (i.e., buttering agents); (2) formation of gel upon mixing with the extraction solvents (i.e., gel forming agents); (3) severe irritation when injected (i.e., irritants); (4) mood depression (e.g., droperidol) or other pronounced central nervous system (CNS) effects; (5) acute gastrointestinal, cardiac or respiratory effects; (6) violent nausea or vomiting; (7) repugnant smells if not used as instructed; (8) sleep inducing, thereby causing the abuser to miss or be made unaware of the euphoria; and/or (9) deactivation or degradation of the active ingredient (i.e., strong oxidation agents (such as hydrogen peroxide), strong acid, or strong base, and/or antagonists) upon attempted extraction. The abuse deterrent agent is employed at about 0.01-10% by weight of the final formulation, preferably about 0.1-4% by weight, and most preferably about 0.1-0.5% by weight.

The abuse deterrent agents can be included in the adhesive drug matrix or in a separate abuse deterrent layer (also referred to as the abuse deterrent matrix). The abuse deterrent layer may be comprised of a combination of polymer and the abuse deterrent agent. Additionally, the abuse deterrent layer can be the abuse deterrent agent itself because many of the recited polymers also act as gel forming agents. Suitable polymers include, but are not limited to, one or more pharmaceutically acceptable polymers that will undergo an increase in viscosity upon contact with a solvent. Preferred polymers include polyethylene oxide, polyvinyl alcohol, hydroxypropyl methylcellulose, carbomers (carbopol), polyvinylpyrrolidone (PVP), and/or other cellulose polymers. In one embodiment of the present invention the polymer includes polyethylene oxide. The polyethylene oxide can have an average molecular weight ranging from about 300,000-5,000,000, and more preferably from about 600,000-5,000,000, and most preferably at least about 5,000,000. In one embodiment, the polyethylene oxide is a high molecular weight polyethylene oxide. Examples of suitable, commercially available polyethylene oxide polymers include Polyox®, WSRN-1105 and/or WSR coagulant, available from Dow Chemical. The preferred weight range of the polymer is from about 1-40% by weight of the final formulation, and the most preferred range of the polymer is from about 2-10% by weight of the final formulation.

Buttering agents are pharmaceutically acceptable bitter substances that create a bitter taste or effect when administered nasally (snorted), orally, buccally or sublingually, making consumption difficult. The bittering agents that may be employed in the present invention include, but are not limited to, sucrose octaacetate (used as a denaturant for alcohol) (e.g., SD-40), denatonium saccharide, denatonium benzoate, caffeine, quinine (or a quinine salt such as quinine sulfate), bitter orange peel oil, and other botanical extract ingredients, such as pepper extract (cubeb), capsicum, and the like. Preferred buttering agents are sucrose octaacetate, denatonium benzoate (Bitrex), and denatonium saccharide (four times more bitter than denatonium benzoate) because they are extremely bitter even at low concentrations and are essentially non-toxic. The bittering agent is employed at about 0.01-10% by weight of the final formulation, preferably about 0.1-4% by weight, and most preferably about 0.1-0.5% by weight.

Gel forming agents are employed to form a gel structure upon mixing with the extraction solvents and, thus, provide abuse deterrent properties. Specifically, gel forming agents are compounds that upon contact with a solvent (e.g., water or alcohol), absorb the solvent and swell, thereby forming a viscous or semi-viscous substance that significantly reduces and/or minimizes the amount of free solvent which can contain an amount of solubilized drug, and which minimizes what can be drawn into a syringe for injection (i.e., IV or intramuscular). The gel can also reduce the overall amount of drug extractable with the solvent by entrapping the drug in a gel matrix. In certain embodiments the gel forming agent can be in a segregated abuse deterrent layer laminated to the adhesive drug matrix.

The gel forming agents that may be employed include, but are not limited to, ethyl cellulose, cellulose acetate, cellulose acetate propionate, cellulose acetate butyrate, cellulose acetate phthalate, cellulose triacetate, cellulose ether, cellulose ester, cellulose ester ether, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyethylmethacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), glycidyl methacrylate copolymers, and mixtures thereof. The gel forming agent is preferably employed at about 3-40% by weight of the final formulation, and the most preferably about 5-20% by weight of the final formulation.

In embodiments of the present invention the gel forming agent includes polyvinyl alcohol with a molecular weight ranging from about 20,000-200,000, specific gravity ranging from about 1.19-1.31, and viscosity ranging from about 4-65 cps. The polyvinyl alcohol used in the formulation is preferably a water-soluble synthetic polymer represented by —(—$C_2H_4O$—)$_n$—, where n can range from about 500-5,000. Examples of suitable, commercially available polyvinyl alcohol polymers include PVA, USP, available from Spectrum Chemical Manufacturing Corporation, New Brunswick, N.J. 08901.

In embodiments of the present invention, the gel forming agent includes hydroxypropyl methyl cellulose (Hypromellose) with a molecular weight ranging from about 10,000-1,500,000, typically from about 5000-10,000 (i.e., low molecular). The specific gravity of the hydroxypropyl methyl cellulose ranges from about 1.19-1.31, with an average specific gravity of about 1.26. Viscosity of the hydroxypropyl methyl cellulose is about 3600-5600 cPs. The hydroxypropyl methylcellulose used in the formulation can be a water-soluble synthetic polymer. Examples of suitable, commercially available hydroxypropyl methylcellulose polymers include Methocel K100 LV and Methocel K4M, available from Dow chemicals.

In other embodiments of the present invention the gel forming agent includes hydrophilic polymers, such as hydrogels, which provides viscosity to the dosage form upon tampering. In such embodiments, when an abuser crushes and dissolves the dosage form in a solvent (e.g., water or saline), a viscous or semi-viscous gel is formed.

In certain embodiments of the present invention, the gel forming agent can include carbomers, having a molecular weight ranging from 700,000-4,000,000 and viscosity ranging from about 4000-39,400 cPs. Carbomer is preferably employed in the present invention from about 1-40% by weight of the final formulation, and most preferably from about 2-10% by weight. Examples of suitable, commercially available carbomers include carbopol 934P NF, carbopol 974P NF, and carbopol 971P NF, available from Lubrizol.

Irritants are pharmaceutically inert compounds that induce irritation to the mucous membranes of the body (i.e., nasal, mouth, eye, intestine, urinary tract). The irritants that may be employed in the present invention include, but are not limited to surfactants, such as sodium lauryl sulfate (SLS), poloxamer, sorbitan monoesters and glyceryl monooleates, as well as spicy ingredients, and others. The irritants are preferably employed at about 0.01-10% by weight of the final formulation, preferably 0.01-10% by weight, and most preferably about 0.1-5% by weight.

In embodiments of the present invention, the irritant can deter abuse upon tampering with the transdermal delivery device. For example, if an abuser extracts and dries the ketamine, then the irritant is exposed and discourages inhalation of the ketamine mixed with the irritant, as inhalation (e.g., via snorting through the nose) will induce pain and/or irritation of the abuser's mucous membrane and/or nasal passageway tissue.

Other suitable excipients useful in the preparation of transdermal delivery devices are within the knowledge of those skilled in the art, and can be found in the Handbook of Pharmaceutical Excipients (7th ed. 2012), the entire content of which is hereby incorporated by reference.

EXAMPLES

Examples 1-5

The formulation of Examples 1-5 are disclosed below in Table 6.

TABLE 6

| Ingredient Class | Ingredient | Ex 1 (wt %) | Ex 2 (wt %) | Ex 3 (wt %) | Ex 4 (wt %) | Ex 5 (wt %) |
|---|---|---|---|---|---|---|
| Active Ingredient | Ketamine | 20 | 25 | 25 | 25 | 25 |
| Pressure-sensitive adhesive | DuroTak 387-2052 | 70 | 65 | | 40 | |
| | DuroTak 87-2677 | | | 55 | | |
| | DuroTak 87-4098 | | | | | 40 |
| Skin permeation enhancer | Oleyloleate | 5 | 5 | 5 | | |
| | Oleyl alcohol | | | | 5 | 5 |
| | Levulinic acid | 5 | 5 | 5 | 5 | 5 |
| | Diethylene glycol monoethyl ether | | | | 5 | 5 |
| Crystallization inhibitors | Polyvinyl pyrrolidone-co-vinyl acetate | | | 10 | 20 | |
| | Polymethacrylate | | | | | 20 |
| Total | | 100 | 100 | 100 | 100 | 100 |

The pressure sensitive adhesive (PSA) employed in Examples 1, 2, and 4 was Duro-Tak 387-2052 (supplied by Henkel Adhesives). The PSA employed in Example 3 was Duro-Tak 87-2677 (Henkel Adhesives). The PSA employed in Example 5 was Duro-Tak 87-4098 (Henkel Adhesives). Persons skilled in the art will understand that other known pressure sensitive adhesives can be readily employed with the transdermal delivery devices of the present invention.

The skin permeation enhancer employed in Examples 4 and 5 was diethylene glycol monoethyl ether, sold under the tradename Transcutol P. Persons skilled in the art will understand that other known skin permeation enhancers can be readily employed with the transdermal delivery devices of the present invention.

The crystallization inhibitor in Examples 3 and 4 was polyvinyl pyrrolidone-co-vinyl acetate, sold under the tradename Kollidon VA 64 (BASF Corporation). The crystallization inhibitor employed in Example 5 was polymathacrylate-based polymer, sold under the tradename Plastoid B (Evonik Corporation). Persons skilled in the art will understand that other known crystallization inhibitor enhancers can be readily employed with the transdermal delivery devices of the present invention.

FIG. 5 is a comparison of the plasma concentration-time profile of a 0.5 mg/kg dose of ketamine in a human subject following: (1) a 40-minute single IV administration; and (2) administration of a 24 hour transdermal delivery device of the present invention according Example 2 (a 9.4 cm² transdermal delivery device with a 3.75 mg/cm² permeation rate). Convolution analysis was applied in accordance with the pharmacokinetic parameters set forth in Fanta, et al., Eur. J. Clin. Pharmacol., 71:441-447 (2015). The transdermal delivery device according to Example 2 exhibits a lower $C_{max}$, preferably less than about 30%, and more preferably less than about 20%, of the $C_{max}$ from an equivalent IV dosage.

FIG. 6 discloses ketamine plasma concentration-time profiles for three sizes (10, 100 and 300 cm²) of the once-a-day transdermal delivery device of the present invention according to Example 2.

FIG. 7 discloses ketamine plasma concentration-time profiles for three sizes (10, 100 and 300 cm²) of the three times-a-day transdermal delivery device of the present invention according to Example 2.

Skin permeation enhancers are incorporated in the transdermal delivery devices of the present invention to ensure that sufficient ketamine can penetrate through skin. Skin permeation studies were performed on the transdermal delivery devices prepared according to Examples 1-5 using Franz diffusion cells maintained at 37° C. The receptor medium was phosphate buffered saline at pH 7.4, the receptor volume was 12 ml and the permeation area was 1.767 cm². Human cadaver skin was used and the tests were performed in triplicate. A 1×1 inch transdermal delivery device was placed onto the donor side of the skin diffusion cells, adhered onto the skin, and the experiment was initiated with the receptor medium being continuously mixed (stirring at 600 rpm). Samples (1.5 ml) of the receptor phase were obtained at 2, 4, 8, 12, 24, 48 and 72 hours. The drug concentrations were quantitated using HPLC. As demonstrated in Table 6, Examples 1-5 of the present invention all provide good skin permeability. The cumulative amounts of ketamine that permeated after 24 hours are shown in Table 7.

TABLE 7

|  | Ex. 1 | Ex. 2 | Ex. 3 | Ex. 4 | Ex. 5 |
|---|---|---|---|---|---|
| Ketamine in transdermal delivery device, mg/cm² | 3.56 | 4.71 | 5.86 | 7.51 | 9.58 |
| 24 h Cumulative Permeation, mg/cm² | 1.21 | 3.72 | 2.62 | 1.74 | 0.73 |

FIG. 8 depicts in vitro skin permeability of the transdermal delivery devices of the present invention according to Example 2 as shown by the Franz Diffusion Cell model.

Drug crystallization will retard drug release and skin permeability, reducing the efficacy of the transdermal delivery device. Drug crystals should not be formed in the transdermal delivery device over a period approximating the shelf life, i.e., for about 6 months or greater. Examples 1 and 2 showed instability, i.e. drug crystals were formed in the adhesive drug matrix 4-7 days after preparation of the transdermal delivery devices. Examples 3, 4 and 5, were found to be stable for at least 4 weeks, i.e. within this period, no crystals were formed. Example 5 was found to be stable for at least 6 months at conditions of 25° C., 60% RH.

Table 8 reports the stability data for the transdermal delivery devices prepared according to Examples 1-5.

Figure 9:
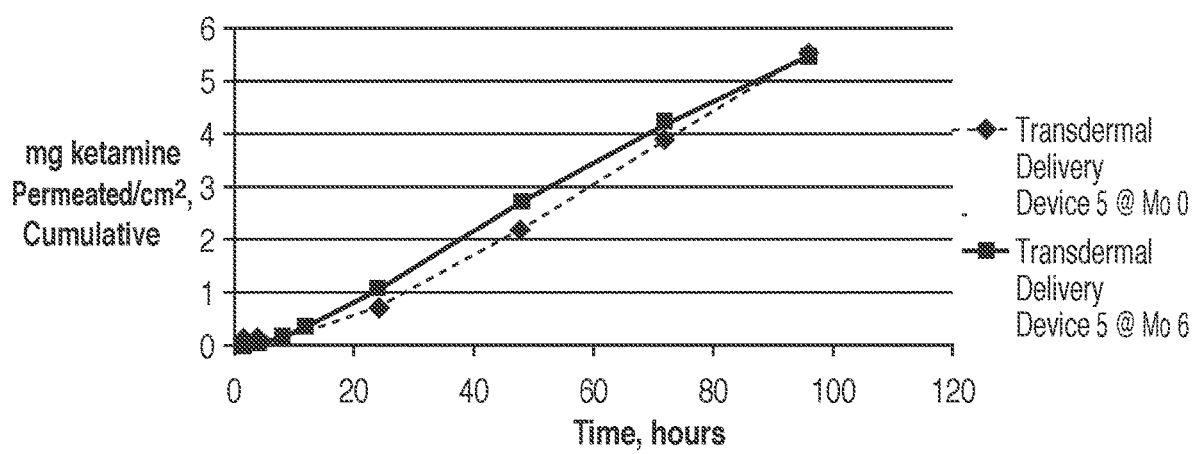
FIG. 9 is a 6-month stability graph of the present invention prepared in accordance with Example 5.
Figure 10:
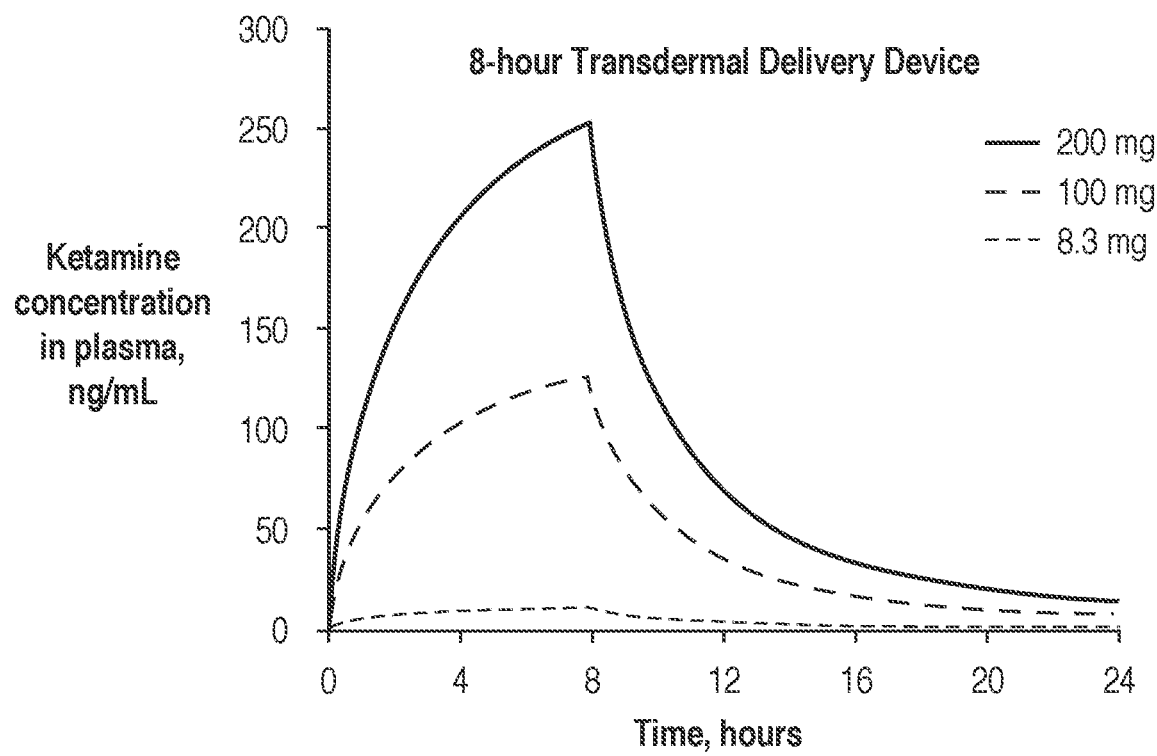
FIGS. 10-13 are ketamine plasma concentration versus time profiles in humans corresponding to the transdermal delivery devices of Table 2. These transdermal delivery devices are for the treatment of MDD. These pharmacokinetic profiles are predicted by known convolution methodology using in vitro transdermal permeation data and in vivo intravenous plasma concentration data.
Figure 11:
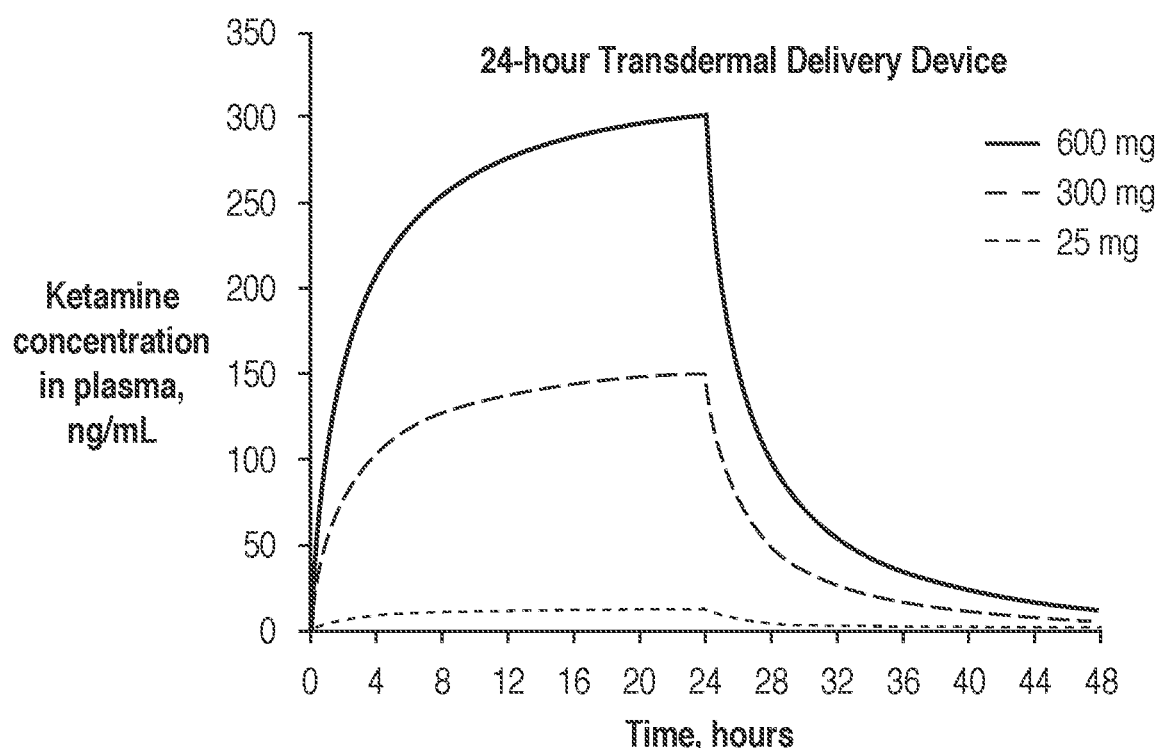
Figure 12:
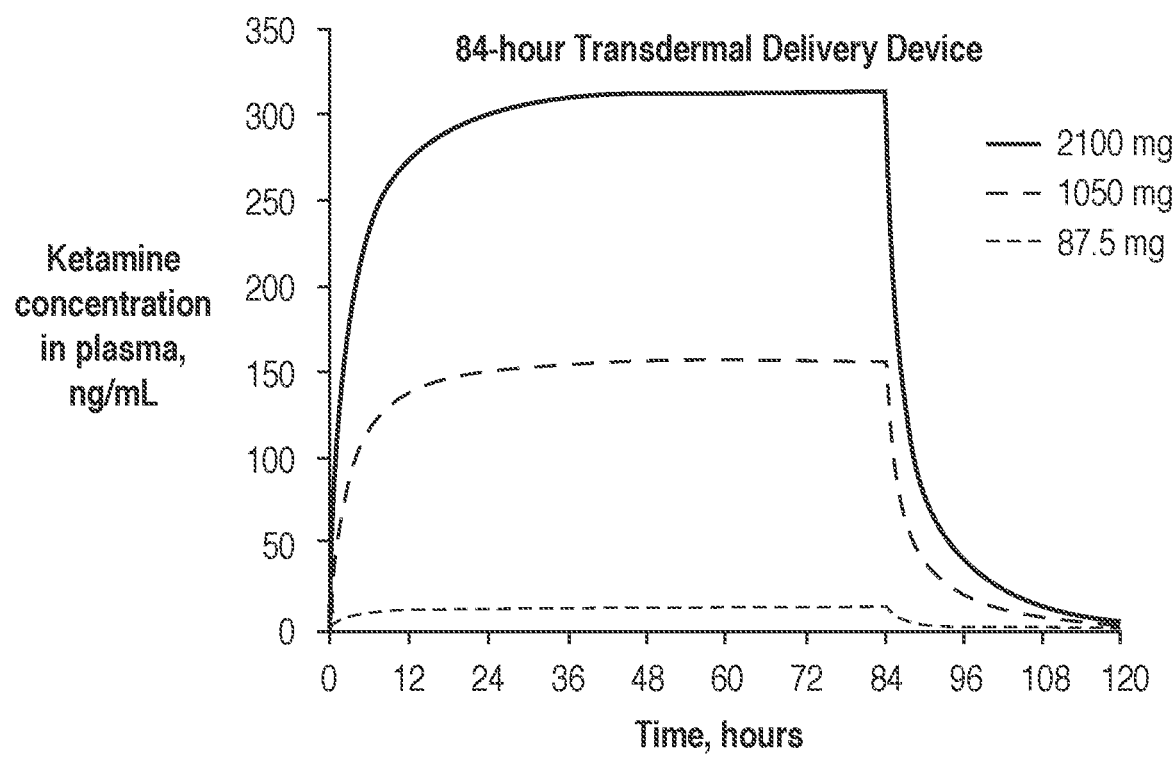
Figure 13:
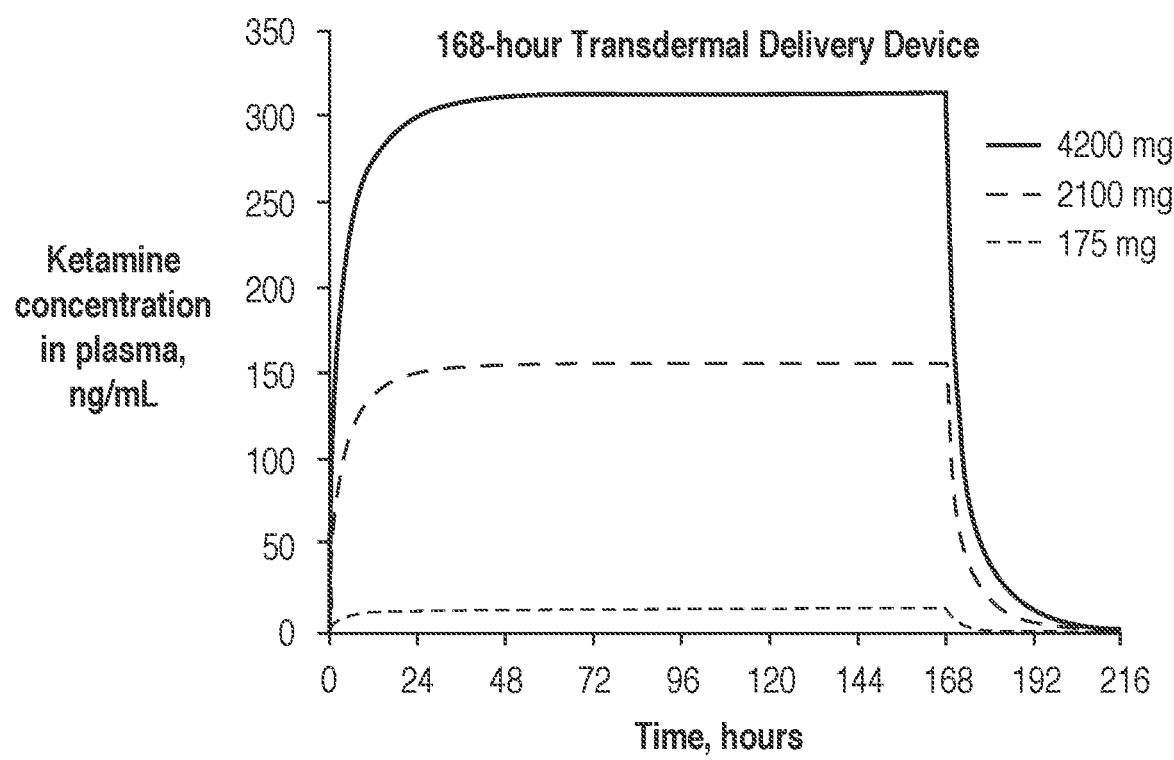
Figure 14:
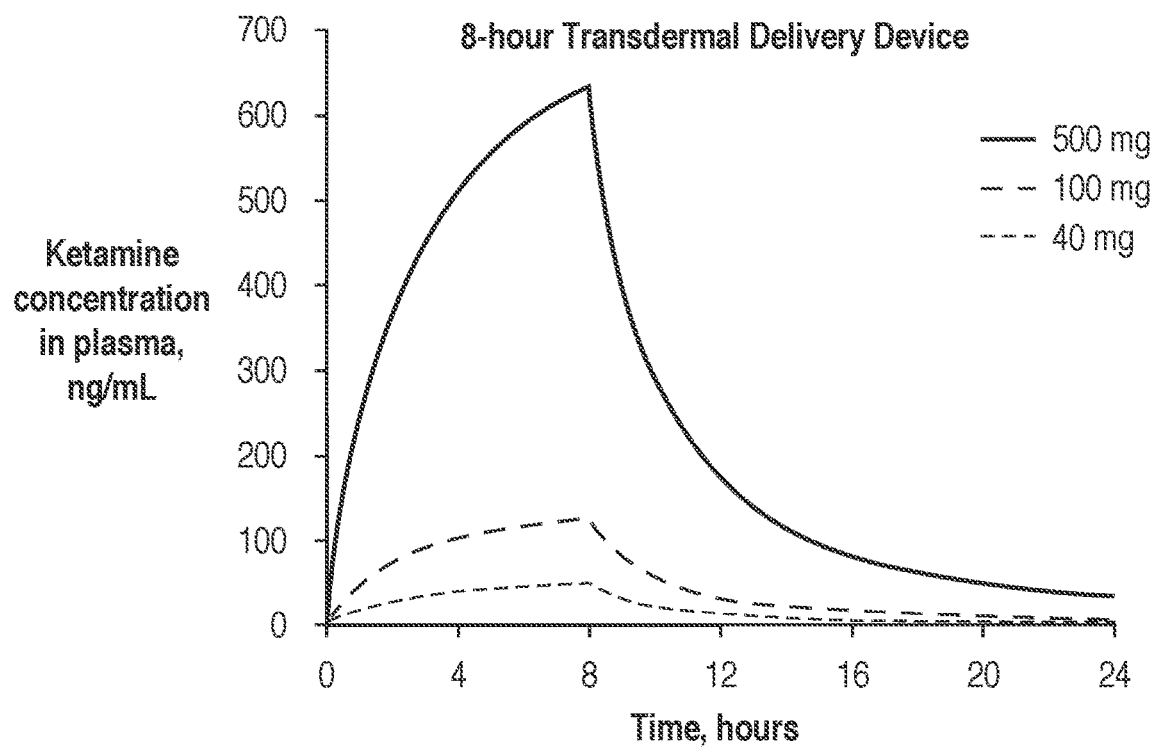
FIGS. 14-17 are graphs of the pharmacokinetic plasma concentrations versus time profiles, corresponding to the transdermal delivery devices of Table 3. These transdermal delivery devices are for the treatment of pain. These pharmacokinetic profiles are predicted by known convolution methodology using in vitro transdermal permeation data and in vivo intravenous plasma concentration data.
Figure 15:
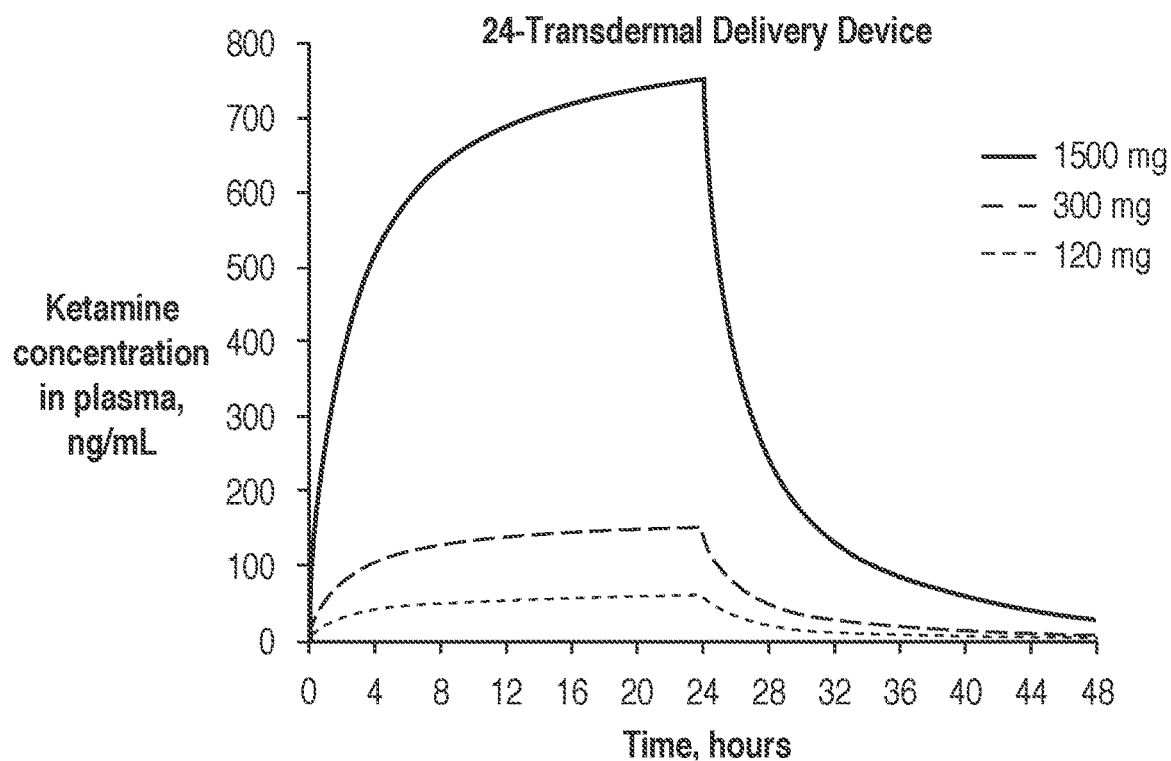
Figure 16:
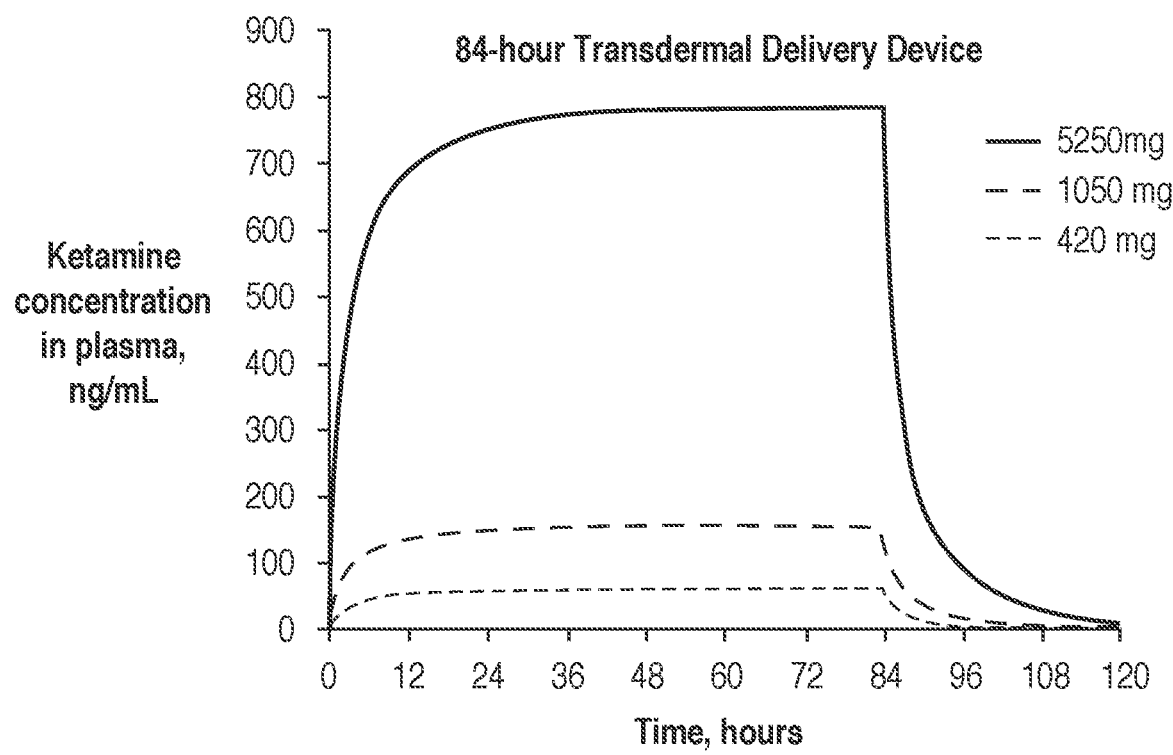
Figure 17:
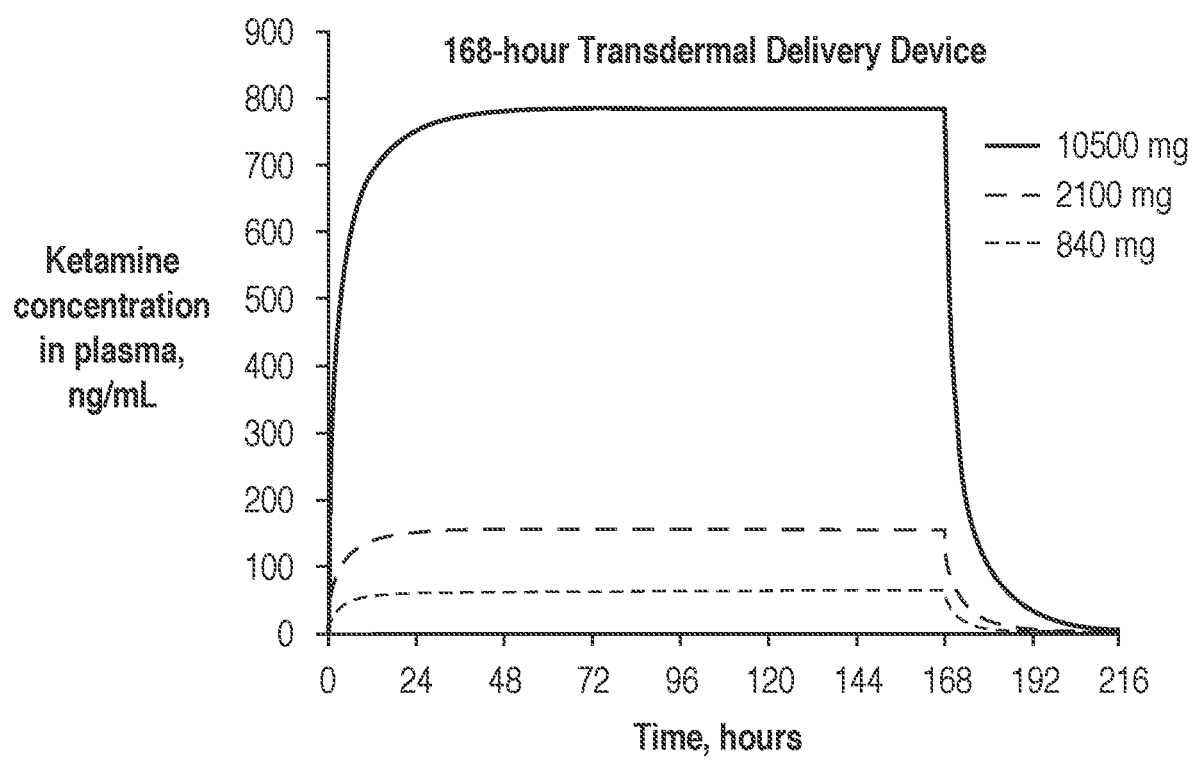

FIG. 9 depicts the stability of ketamine in a transdermal delivery device according to Example 5 after 0 months and after 6 months.

TABLE 8

|  | Ex 1 | Ex 2 | Ex 3 | Ex 4 | Ex 5 |
|---|---|---|---|---|---|
| Crystallization Inhibitors | None | None | 10% Kollidon VA 64 | 20% Kollidon VA 65 | 20% Plastoid B |
| Stability at 25° C./ 65% RH | Crystals formed at Day 10 | Crystals formed at Day 10 | Crystals formed at Month 3 | Crystals formed at Month 3 | No crystals formed up to Month 6 |

Example 6

Transdermal Delivery Device with Non-Segregated Abuse Deterrent Agents

Example 5 was modified to prepare a transdermal delivery device that contains 5 mg of denatonium benzoate and 200 mg of ketamine in the adhesive drug matrix. In vitro skin permeation studies showed that no denatonium benzoate permeated the skin (because of its large molecular weight (447 DA) and the high melting point (170° C.). Nevertheless, ketamine showed excellent skin permeability (0.8 mg/cm² in 24 hours), indicating that incorporation of an abuse deterrent agent, such as denatonium benzoate did not affect the skin permeation of ketamine.

In an extraction study to simulate attempted drug-abuse, transdermal delivery devices prepared according to Example 6 were soaked for 60 minutes in 100 ml of three different media: (1) 40% ethanol; (2) 70% isopropyl alcohol; and (3) acetone. All three media were assayed for ketamine and denatonium benzoate using HPLC. More than 50% of the original ketamine and more than 50% of the denatonium benzoate were found in the media (i.e., the bittering agent extracted proportionally to the amount of ketamine extracted), indicating the effectiveness of using denatonium benzoate as an abuse deterrent agent in the present invention.

Example 7

Transdermal Delivery Device with Abuse Deterrent Agents in a Segregated Layer

Example 7 comprises a transdermal delivery device with an abuse deterrent agent in a segregated layer. The abuse deterrent agent employed in Example 7 is a gelling agent which reacts with common solvents (e.g., water and alcohol) used to extract and abuse the ketamine in the transdermal delivery device. The thickness of the adhesive-drug layer and the abuse deterrent layer are both about 2 to about 5 mils. The transdermal delivery device according to Example 7 is prepared in a two-step process.

Step 1. Preparation of the Abuse Deterrent Layer

PolyOx 1105, propylene glycol, and PEG 4000 were mixed to form the abuse deterrent layer. The three ingredients were dissolved in a water/ethanol solvent, followed by casting of the wet film directly on a sheet of backing layer, e.g., 3M's polyethylene film, Scotpak 1012. The wet film is then dried at 60° C. for 30 min in a convective-air drying oven. The coating thickness of the abuse deterrent layer is about 3 mils. An example of a suitable abuse deterrent layer composition is disclosed in Table 9.

TABLE 9

| Ingredient | gm | Wt % |
| --- | --- | --- |
| PolyOx WSR N-10 | 7.20 | 46.2% |
| PolyOx 1105 | 3.60 | 23.1% |
| PEG 4000 | 2.80 | 17.9% |
| Propylene Glycol | 2.00 | 12.8% |
| Ethanol Anhydrous* | 28.00 | 0.00% |
| Purified Water* | 57.00 | 0.00% |
| Total | 100.60 | 100% |

*evaporated during processing.

An abuse deterrent agent, such as Bitrex and sodium lauryl sulfate (SLS), may be incorporated into the abuse deterrent layer, preferably from about 0.01-5% by weight of the final formulation, and most preferably from about 0.05-0.5% by weight of the final formulation.

Step 2. Preparation of Adhesive Drug Matrix Layer:

The adhesive drug matrix layer is prepared by casting the adhesive drug matrix mix directly on the abuse deterrent layer (prepared in step 1), or onto a release liner and then laminated to the abuse deterrent layer.

DuroTak 87-4098 is weighed into a 100 ml beaker, and then mixed at low speed. Next, the Kollidon VA 64 and the ketamine are added to the mixer. The batch is mixed until all ingredients are dissolved. Then wet films are prepared at 3 mils thickness using a film casting applicator on release liner, such as 3M's 9744. The wet coating is air dried for 1 hour, and then oven dried at 60° C. for 10 min. Finally, the laminate is dried onto the abuse deterrent layer, which was subsequently coated on 3M's backing Scotpak 1012.

The laminated sheet can be die-cut into transdermal delivery devices of various sizes, such as 10 cm², 20 cm², 100 cm², 300 cm² to obtain the desired dosages of the drug.

An exemplary composition of the adhesive drug matrix is given in Table 10.

TABLE 10

| Ingredients | Wt % |
| --- | --- |
| Ketamine | 15% |
| vinylpyrrolidone-vinyl acetate copolymers (Kollidon VA 64) | 20% |
| DuroTak 87-4098 | 65% |
| Total | 100% |

Example 8

A transdermal delivery device according to Examples 7 is prepared with apomorphine, an emetic, in the abuse deterrent layer. After solvent extraction by an abuser, the emetic can cause severe nausea if injected, snorted, or inhaled. Apomorphine is preferably employed in the present invention from about 0.05-5% by weight of the final formulation, and most preferred from about 0.1-2% by weight.

Example 9

Example 9 was prepared in accordance with Example 7, with the exception that the abuse deterrent agent is capsaicin. After being dissolved in solvents by an abuser, the ketamine solution containing capsaicin will cause a torturous burning sensation if snorted or inhaled, thereby reducing the abuse potential of the transdermal drug delivery device.

Examples 10

Table 11 provides additional techniques by which the abuse deterrent agents can be employed in the transdermal delivery device of the present invention.

TABLE 11

| Potential Route of Manipulation/Abuse | Abuse Deterrent Agents |
| --- | --- |
| Extraction with drinkable solvent (alcohol), followed by drinking | Denatonium released when abused, co-precipitates with ketamine, and bitters the drinkable solvent |
| Extraction with injectable medium, followed by injection | Gel forming agent will dissolve in medium, forming viscous liquid, which deters injection |
| Extraction with solvent, evaporation, followed by snorting | SLS will co-precipitate with ketamine, and cause nasal mucosal irritation upon snorting |
| Extraction with solvent, evaporation, followed by mixing with liquid and drinking | Denatonium released when abused, co-precipitates and dries with ketamine, and bitters the subsequent drinking liquid |

Example 11

In an embodiment of the present invention is prepared according to Example 7, in which the adhesive-drug layer comprises an adhesive and 200 mg of ketamine, and the abuse deterrent layer comprises a gel forming agent comprising 7 mg of SLS and 5 mg of denatonium benzoate.

The foregoing description and examples have been set forth merely to illustrate the present invention and are not intended to be limiting. Since modifications of the described embodiments incorporating the spirit and substance of the invention may occur to persons skilled in the art, the invention should be construed broadly to include all variations within the scope of this application, including but not limited to the appended claims and equivalents thereof.

The invention claimed is:

1. A transdermal delivery device comprising ketamine, which is a drug-in-adhesive patch comprising a backing layer, an adhesive-drug layer, and a release liner, wherein the adhesive-drug layer comprises:
   a) ketamine of 10-25% by weight,
   b) a pressure sensitive adhesive in an amount of about 40-60% by weight,
   c) a combination of oleyl oleate and levulinic acid or a combination of oleyl alcohol, levulinic acid, and diethylene glycol monoethyl ether, and
   d) a polyvinyl pyrrolidone-co-vinyl acetate or a polymethylacrylate-based polymer,
   wherein ketamine is the only active ingredient in the transdermal delivery device, wherein the transdermal delivery device provides a ketamine permeation rate of about 0.1-5 mg/day/cm² of ketamine for about 8 hours to 168 hours.

2. A method of treating major depressive disorders comprising administering the transdermal delivery device according to claim 1 to a human, wherein the administering provides a plasma concentration of ketamine ranging from about 10-200 ng/ml for about 8-168 hours.

3. The method according to claim 2 wherein the administering provides a plasma concentration of ketamine ranging from about 10-100 ng/ml for about 8-168 hours.

4. A method of treating pain comprising administering the transdermal delivery device according to claim 1 to a human, wherein the administering provides a plasma concentration of ketamine ranging from about 50-1000 ng/ml for about 8-168 hours.

5. The method according to claim 4 wherein the administering provides a plasma concentration of ketamine of about 500 ng/ml for about 8-168 hours.

6. The transdermal delivery device according to claim 1, which provides a ketamine permeation rate of about 0.5-5 mg/day/cm² of ketamine for about 1 day, 3.5 days, or 7 days.

7. The transdermal delivery device according to claim 1, wherein said device is about 10-300 cm².

8. The transdermal delivery device according to claim 7, wherein said device is about 10-100 cm².

9. The transdermal delivery device according to claim 1, wherein the transdermal delivery device provides reduced $C_{max}$ compared to immediate release administration of ketamine at equivalent doses.

10. The transdermal delivery device according to claim 1 which provides reduced plasma fluctuations over time when compared with plasma concentrations from immediate release ketamine formulations.

11. The transdermal delivery device according to claim 1, which provides:

(a) reduced $C_{max}$ fluctuations, (b) reduced plasma concentration fluctuations, and (c) reduced adverse side effects, when compared with ketamine plasma concentrations from immediate release formulations at equivalent doses.

12. The transdermal delivery device according to claim 1, which provides a $C_{max}$ no greater than about 30% of the $C_{max}$ from a dose equivalent immediate release ketamine formulation.

13. The transdermal delivery device according to claim 1, wherein said ketamine is the R-enantiomer or S-enantiomer.

\* \* \* \* \*